United States Patent
Puca et al.

(10) Patent No.: US 11,891,421 B2
(45) Date of Patent: *Feb. 6, 2024

(54) VARIANT OF A BPIFB4 PROTEIN

(71) Applicant: ROXIANT APS, Copenhagen (DK)

(72) Inventors: Annibale Alessandro Puca, Naples (IT); Carmine Vecchione, Villapiana Scalo (IT)

(73) Assignee: LGVI S.R.L., Naples (IT)

( * ) Notice: Subject to any disclaimer, the term of this patent is extended or adjusted under 35 U.S.C. 154(b) by 165 days.

This patent is subject to a terminal disclaimer.

(21) Appl. No.: 17/525,531

(22) Filed: Nov. 12, 2021

(65) Prior Publication Data
US 2022/0169686 A1  Jun. 2, 2022

Related U.S. Application Data

(63) Continuation of application No. 16/511,051, filed on Jul. 15, 2019, now Pat. No. 11,208,447, which is a
(Continued)

(30) Foreign Application Priority Data

Dec. 28, 2012  (EP) .................................... 12425208

(51) Int. Cl.
*C07K 14/47*  (2006.01)
*C12N 15/86*  (2006.01)
(Continued)

(52) U.S. Cl.
CPC .......... *C07K 14/47* (2013.01); *C07K 14/4742* (2013.01); *C12N 15/81* (2013.01); *C07K 2319/20* (2013.01); *C12N 2015/8518* (2013.01)

(58) Field of Classification Search
CPC ...... A61K 38/1751; A61P 11/00; A61P 13/12; A61P 15/00; A61P 15/10; A61P 25/00; A61P 25/28; A61P 27/02; A61P 27/06; A61P 27/12; A61P 29/00; A61P 3/06; A61P 3/10; A61P 35/00; A61P 43/00;
(Continued)

(56) References Cited

U.S. PATENT DOCUMENTS 11,208,447 B2 * 12/2021 Puca .......................... A61P 3/06
2003/0124582 A1 * 7/2003 Grell ....................... A61P 31/04
435/325

FOREIGN PATENT DOCUMENTS

CN   101631861   1/2010
JP   2011231022   11/2011
(Continued)

OTHER PUBLICATIONS

Bianca et al.,"Endogenous urotensin II selectively modulates erectile function through eNOS", PLoS One (2012), 7(2):e31019; Feb. 2012.
(Continued)

*Primary Examiner* — Randall L Beane
(74) *Attorney, Agent, or Firm* — Hoffmann & Baron, LLP

(57) ABSTRACT

The present invention relates to a variant of BPIFB4 protein (Bactericidal/Permeability Increasing protein family B, member 4) and to a polynucleotide or a vector encoding said variant of BPIFB4 protein and to their use for the treatment of pathologies involving impairment of nitric oxide signalling.

13 Claims, 13 Drawing Sheets
Specification includes a Sequence Listing.

Related U.S. Application Data continuation of application No. 14/655,651, filed as application No. PCT/EP2013/078076 on Dec. 27, 2013, now abandoned.

(51) Int. Cl.
  *C12N 15/85* (2006.01)
  *C12N 15/81* (2006.01)

(58) Field of Classification Search
  CPC ...... A61P 7/02; A61P 9/00; A61P 9/10; A61P 9/12; C07K 14/47; C07K 14/4742; C07K 2319/20; C12N 15/86; C12N 2015/8518; C12N 2710/10343; C12N 2750/14143
  See application file for complete search history.

(56) References Cited

FOREIGN PATENT DOCUMENTS

| | | |
|---|---|---|
| WO | 01/79269 A2 | 10/2001 |
| WO | 02/063008 A2 | 8/2002 |
| WO | 03/052052 A2 | 6/2003 |
| WO | 05/033321 A2 | 4/2005 |
| WO | 2006/022619 A2 | 3/2006 |
| WO | 2007/140474 A2 | 12/2007 |
| WO | 2008/073915 | 6/2008 |
| WO | 09/013290 A1 | 1/2009 |
| WO | 10/071832 A1 | 6/2010 |
| WO | 12/112832 A1 | 8/2012 |
| WO | 13/151668 A2 | 10/2013 |

OTHER PUBLICATIONS

Li et al., "Improvement of vascular function by acute and chronic treatment with theGPR30 agonist G1 in experimental diabetes mellitus", PLoS One (2012), 7(6):e38787; Jun. 2012.
Ponnuswamy et al., "eNOS protects from atherosclerosis despite relevant superoxide production by the enzyme in apoE mice", PLoS One (2012), 7(1):e30193, Jan. 2012.
Puca et al., Endothelial nitric oxide synthase, vascular integrity and human exceptional longevity, Immunity & Ageing, 2012, 9(26): 1742-493, Nov. 2012.
Savard et al., "eNOS gene delivery prevents hypertension and reduces renal failure and injury in rats with reduced renal mass", Nephrol DialT ransplsnt 27(6):2182-2190, (Jun. 2012).
Schoeb et al., "Endothelial nitric oxide synthase inhibits the development of autoimmune-mediated vasculitis in mice", Arthritis Rheum 64(12):4114-4124, (Dec. 2012).
SU et at., Bradykinin restores left ventricular function, sarcomeric protein phosphorylation, and e/eNOS levels in dogs with Duchenne muscular dystrophy cardiomyopathy, Cardiovasc Res 95(1):86-96 (Jul. 2012).
Plaza-Plaza et al., "P{harmacolgenetic polymorphisms contributing to toxicity induced by methotrexate in the southern spanish population with rheumatoid arthritis", Omics, 16 p. 589-595, (Nov. 2012).
International Search Report and the Written Opinion, International Searching Authority: European Patent Office, dated Apr. 2, 2014, for International Application No. PCT/EP2013/078076, 11 pages.
Andrault et al., "Expansion of the BPI family by duplication on human chromosome 20: characterization of the RY gene cluster in 20q11.21 encoding olfactory transporters/antimicrobial-like peptides", Genomic (Aug. 2003), 82(2):172-84.
Babizhayev, "Bioactivation antioxident and transglycating properties of N-acetylcarnosine autoinduction prodrug of a dipeptide L-carnosine in mucoadhesive drug delivery eye-drop formulation: powerful eye health application technique and therapeutic platform", Drug Test Anal (Jun. 2012), 4(6):468-85.
Bingle et al., "Phylogenetic and evolutionary analysis of the PLUNC gene family", Protein Science (Feb. 2004), 13(2):422-30.
Bingle et al., "PLUNG: a novel family of candidate host defence proteins expressed in the upper airways and nasopharynx", Human Molecular Genetics (Apr. 2002), 11(8):937-43.
Bingle, et al., "Systematic nomenclature for the PLUNC/PSP/BSP30/SMGB proteins as a subfamily of the BPI fold-containing superfamily", Biochem Soc Trans (Aug. 2011), 39(4):977-83.
Böger et al., "Plasma asymmetric dimethylarginine and incidence of cardiovascular disease and death in the community", Circulation (Mar. 2009), 119(12):1592-600.
Chiou, "Review: effects of nitric oxide on eye diseases and their treatment", J Ocul Pharmacol Ther (Apr. 2001), 17(2):189-98.
D'Uscio, "eNOS uncoupling in pulmonary hypertension", Cardiovascular Research (Dec. 2011), 92(3):359-60.
Diaz-Fernandez et al., "Multicomponent polymeric micelles based on polyaspartamide as tunable fluorescent pH-window biosensors", Biosens Bioelectron (Sep. 2010), 26(1):29-35.
Faraci, "Protecting the brain with eNOS: run for your life", Circulation Research (Nov. 2006), 99(10):1029-30.
Förstermann et al., "Endothelial nitric oxide synthase in vascular disease: from marvel to menace", Circulation (Apr. 2006), 113(13):1708-14.
Javadi-Paydar et al., "Atorvastatin improved scopolamine-induced impairment in memory acquisition in mice: involvement of nitric oxide", Brain Res (Apr. 2011), 1386:89-99.
Jiang et al., "Overexpression of endothelial nitric oxide synthase improves endothelium-dependent vasodilation in arteries infused with helper-dependent adenovirus", Hum Gene Ther (Nov. 2012), 23(11):1166-75.
Kanwar et al., "Recent advances on the roles of NO in cancer and chronic inflammatory disorders", Curr Med Chem (2009), 16(19)2373-94.
Kinane et al., "Human Variability in Innate Immunity", Periodontology (2007), 45:14-34.
Kleindorp et al., "Candidate gene study of FOX01, FOX04, and FOX06 reveals no association with human longevity in Germans", Aging Cell (Aug. 2011), 19(4):622-8.
Kobayashi et al., "Sarcolemma-localized nNOS is required to maintain activity after mild exercise", Nature (Nov. 2008), 456(7221):511-5.
Kwak et al., "Exogenou nitric oxide inhibits experimental autoimmune uveoretinitis development in Lewis rats by modulation of the Th1-dependent immune response", Mol Cellls (Oct. 2001). 12(2):178-84.
Lee et al., "Selective PPAR modulator INT131 normalize insulin signaling defects and improves bone mass n diet-induced mice", Am J Physiol Endocrinol Metab (Jan. 2012), 302:E552-E560.
Lemarié et al.,. "Mthfr deficiency induces endothelial progenitor cell senescence via uncoupling of eNOS and downregulation of SIRT1", Am J Physiol Heart Circ Physiol (Mar. 2011), 300(3);H745-53.
Li et al., "Diabetic eNOS-knockout mice develop accelerated retinopathy", Invest Ophthalmol Vis Sci 51(10):5240-5246, (2010).
Loscalzo, "Nitric oxide insufficiency, platelet activation and arterial thrombosis", Circ Res (Apr. 2001), 88(8):756-62.
Madden, "Role of the vascular endothelium and plaque in acute ischemic stroke", Neurology (Sep. 2012), 79(13 Suppl):S58-62.
Malovini et al., "Association study on long-living individuals from Southern Italy identifies rs10491334 in the CAMKIV gene that regulates survival proteins", Rejuvenation Res (Jun. 2011), 14(3)283-91.
Miyamoto et al., "Replication protein A1 reduces transcription of the endothelial nitric oxide synthase gene containing a-786T—>Cmutation associated with coronary spastic angina", Hum Mol Genet (Nov. 2000), 9(18):2629-37.
Moustafine et al., "Drug release modification by interpolymer interaction between countercharged types of Eudagit RL 30D and FS 30D in double-layer films", Int J Pharm (Dec. 2012), 439(1-2):17-21.
Murano et al., "Hyaluronan: from biomimetic to industrial business strategy", Nat Prod Commum (Apr. 2011), 6(4):555-72.
Nakata et al., "Spontaneou myocardial infarction in mice lacking all nitric oxide synthase isoforms", Circulation (Apr. 2008), 117(17):2211-23.

(56) References Cited

OTHER PUBLICATIONS

Quyyumi et al., "Contribution of nitric oxide to metabolic coronary vasodilation in the human heart", Circulation (Aug. 1995), 92(3):320-6.
Rayatnia et al., "Nitric oxide involvement in consolidation, but not retrieval phase of cognitive performance enhanced by atorvastatin in mice", Eur J Pharmacol (Sep. 2011), 666(1-3): 122-30.
Rothe et al., "Rapid Construction of Adeno-Associated Virus Vectors Expressing Multiple Short Hairpin RNAs with High Antiviral Activity Against Echovirus 30", Oligonucleotides (2010), 20(4) 191-198.
Roy et al., "I-TASER: a unified platform for automated protein structure and function prediction", Nat Protoc (Apr. 2010), 54(4): 725-38.
Savvidou et al., "Endothelial dysfunction and raised plasma concentrations of asymmetric dimethylarginine in pregnant women who subsequently develop pre-eclapsia", Lancet (May 2003), 361(9368): 1511-7.
Sharif et al., "Gene-eluting tents: abenovirus-mediated delivery if eNOS to the blood vessel wall accelerates re-endothelialization and inhibits restenosis", Mol Ther (Oct. 2008), 16(10): 1674-80.
Sparacino-Watkins et al., "Nitrate-nitrile-nitric oxide pathway in pulmonary arterial hypertension therapeutics", Circulation (Jun. 2012), 125(23)2824-6.
Tousoulis et al., "The role of nitric oxide on endothelial function", Curr Vasc Pharmacol (Jan. 2012), 19(1):4-18.
Varadi et al., "Novel random peptide libraries displayed on AAV serotype 9 for selection of endothelial cell-directed gene transfer vectors", Gene Ther (Aug. 2012), 19(8):800-9.
Vecchione et al.,"Protection from angiotensin II-mediated vasculotoxic and hypertensive response in mice lacking PI3Kgamma", J Exp Med (Apr. 2005), 201(8); 1217-28.
Vita, "Endothelial function", Circulation (Dec. 2011), 124(25):e90.
Wu et al., "Endothelial NOS-deficient mice reveal dual roles for nitric oxide during experimental autoimmune encephalomyelitis", Glia (Aug. 2009), 57(11): 1204-15.
Zincarelli et al., "Analysis of AAV serotypes 1-9 mediated gene expression and tropism in mice after systemic injection", Mol Ter (Jun. 2008), 16(6):1073-80.
Vecchione et al., "A rare genetic variant of BPIFB4 predisposes to high blood pressure via impairment of nitric oxide signaling", Scientific Reports, Aug. 29, 2018, pp. 1-10, 7:9706, Italy.
Fuguo, et al., "Relationship between nitric oxide and nitric oxide synthase and cutaneous vasculitis", with English translation thereof, J. Dermatol., 2004, 37(6), p. 361.
Qinghuai et al., "The effect of nitrogen monoxide and its synthase on the diabetic retinal damage", with English translated Abstract, J. of Ophthalmol., 2005, 41(9) p. 837.
Hermans et al., Reducing residual vascular risk in patients with atherogenic dyslipidemia: where do we go from here?, Clinical Lipidology, 5-6, 811-826, 2010.
The ACCIRD Study Group, "Effects of Combination Lipid Therapy in Type 2 Diabetes Mellitus", N Engl J Med 2010,362: 1563-74.
Mimoun et al., "Retinal microvascularisation abnormalities and cardiovascular risk", Arch. Cardiovasc. Dis. (2009) 102 p. 449-446.
Schultz et al., "Recombinant adeno associated virus trnasduction and integration", Mol. Ther. (2008) 16(7) p. 1189-1199.
Beamer et al., "The BPI/LBP family of proteins: A structural analysis of conserved regions", Protein Science, 7:906-914, (1998).
Kleiger et al., "The 1.7 A Crystal Structure of BPI: A Study of How Two Dissimilar Amino Acid Sequences can Adopt the Same Fold", J. Mol. Biol. 299, 1019-1034, (2000).
Qui Xiayang et al., "Crystak structure of cholesteryl ester transfer protein reveals a long tunnel and four bound lipid molecules", Nat. Structure & Molecular Biology, 14(2): 106-113, (2007).
Burnett, A., "The role of nitric oxide in erectile dysfunction: implications for medical therapy", J Clin ypertens,8(12 Suppl 4):53-62, (2006).
Duplain et al., "Insulin resistance, hyperlipidemia, and hypertension in mice lacking endothelial nitric oxide synthase", Circulation, 104(3):342-345, (2001).
Eberhardt et al., "Chronic venous insufficiency", Circulation, 111(18):2398-2409, (2005).
Heil et al., "The 894 G > T variant of endothelial nitric oxide synthase (eNOS) increases the risk of recurrent various thrombosis through interaction with elevated homocysteine levels", JThromb Haemost, 2(5):750-753 (2004).
Huang, P., "eNOS, metabolic syndrome and cardiovascular disease", Trends Endocrinol Metab 20(6):295-302, (2009).
Kugiyama et al., "Nitric oxide activity is deficient in spasm arteries of patients with coronary spastic angina", Circulation, 94(3):266-271, (1996).
Linares et al., Neuronal nitric oxide synthase plays a key role in CNS demyelination:, J Nerosci 26(49):12672-12681, (2006).
Shimasaki et al., "Association of the missense Glu298Asp variant of the endothelial nitric oxide synthase gene with myocardial infarction", J Am Coll Cardion 31(7):1506-1510, (1998).
Hunt, J., "An introduction to cancer", available online at http://www.medschool.lsuhsc.edu/genetics_center/louisiana/article_cancer.htm,downloaded Jul. 18, 2016.
Sunada et al., "Transgenic mice expressing mutant caveolin-3 show severe myopathy associated with increased nnos activity", Human Mol. Gen. (2001) 10(3) p. 173-178.
Yampolsky et al., "Theexchangeability of amino acids in proteins", Genetics (2005) 170 p. 1459-1472.
Brown, G., "Nitric oxide and mitochondria", Frontiers in Bioscience (2007) 12 p. 1024-1033.
Paget et al., "Infectibility of endovascular stents following antibiotic prophylaxis or after arterial wall incorporation", Am. J. Surg. (1999) 178 p. 219-224.
Zhou et al., "Statins and cardiovascular diseases: from cholesterol lowering to pleiotropy", Curr. Pharm. Des. (2009) 15(5) p. 476-478.
Kannel et al., "Is the relation of systolic blood pressure to risk of cardiovascular disease continuous and grade, or are there critical values?", Hypertension (2003) 42(3) p. 453-457.
Nguyen et al., "Retinal vascular changes in pre-diabetes an pre-hypertension—new findings and their research and clinical implications", Diabetes Care (2007) p. 1-20.
Brown, W. Virgil, "Expert commentary: the safety of fibrates in lipid lowering therapy", Am. J. Cardiol. (2007) 99 (suppl) p. 19C-21C.

\* cited by examiner

Figure 1-1 ttcgagctcgcccgacattgattattgactagttattaata
gtaatcaattacggggtcattagttcatagcccatatatgg
agttccgcgttacataacttacggtaaatggcccgcctggc
tgaccgcccaacgaccccgcccattgacgtcaataatgac
gtatgttcccatagtaacgccaatagggactttccattgac
gtcaatgggtggagtatttacggtaaactgcccacttggca
gtacatcaagtgtatcatatgccaagtacgcccctattga
cgtcaatgacggtaaatggcccgcctggcattatgcccagt
acatgaccttatgggactttcctacttggcagtacatctac
gtattagtcatcgctattaccatggtgatgcggttttggca
gtacatcaatgggcgtggatagcggtttgactcacgggat
tccaagtctccaccccattgacgtcaatgggagtttgttt
tggcaccaaaatcaacgggactttccaaaatgtcgtaacaa
ctccgccccattgacgcaaatgggcggtaggcgtgtacggt
gggaggtctatataagcagagctcgtttagtgaaccgtcag
atcgcctggagacgccatccacgctgttttgacctccatag
aagacaccgggaccgatccagcctccgcggccgggaacggt
gcattggaacgcggattcccgtgccaagagtgacgtaagt
accgcctatagagtctataggcccacccccttggcttgtt
agaacgcggctacaattaatacataaccttatgtatcatac
acatacgatttaggtgacactatagaataacatccactttg
cctttctctccacaggtgtccactcccaggtccaactgcac
ctcggttctaagcttgcatgctgcaggtcgactctagagg
atccccgccaccatgctgcagcaaagtgatgctctcactc
ggcctgagagaggtgccttgggtgttggtgatattccct
acaatgacttcatgtccgaggaccccccagtatatacc
aacggcaaaaacttgatggtatttaccagtatggtcacat
tgagaccaacgacaacactgctcagctgggggcaaatacc
gatatggtgagatccttgagtccgagggaagcatcaggac

Figure 1-2 ctccgaaacagtggctatcgcagtgccgagaatgcatatgg
aggccacagggcctcgggcgatacagggcagcacctgtgg
gcaggcttcaccggcgagagctgcagcctggagaaatccca
cctggagttgccactggggcggtgggccaggtggtttgct
gggcactggaggcatgctggcagctgatggcatcctcgcag
gccaaggtggcctgctcggcggaggtggtctccttggtgat
ggaggacttcttggaggagggggtgtcctgggcgtgctcgg
cgagggtggcatcctcagcactgtgcaaggcatcacggggc
tgcgtatcgtggagctgaccctccctcgggtgtccgtgcgg
ctcctgccggcgtgggtgtctacctgagcttgtacacccg
tgtggccatcaacgggaagagtcttattggcttcctggac**a
/g**tcgcagtagaagtgaacatcacagccaaggtccggctga
ccatggaccgcacgggttatcctcggctggtcattgagcga
tgtgacacctcctaggggcatcaaagtcaagctgctgcg
agggcttctccccaatctcgtggacaatttagtgaa/cccg
agtcctggccgacgtcctccctgacttgctctgccccatcg
tggatgtggtgctgggtcttgtcaatgaccagctgggcctc
gtggattctctgattcctctggggatattgggaagtgtcca
gtacacttctccagcctcccgcttgtgaccggggaattcc
tggagctggacctcaacacgctggttggggaggctggagga
ggactcatcgactacccattggggtggccagctgtgtctcc
caagccgatgccagagctgcctcccatgggtgacaacacca
agtcccagctggccatgtctgccaacttcctgggctcagtg
ctgactctactgcagaagcagcatgctctagacctggatat
caccaatggcatgtttgaagagcttcctccacttaccacag
ccacactgggagccctgatccccaaggtgttccagcagtac
ccgagtcctgcccacttatcatcaggatccaggtgctgaa
cccaccatctgtgatgctgcagaaggacaaagcgctggta
aggtgttggccactgccgaggtcatggtctcccagcccaaa

Figure 1-3 gacctggagactaccatctgcctcattgacgtggacacaga
attcttggcctcatttccacagaaggagataagctcatga
ttgatgccaagctggagaagaccagcctcaacctcagaacc
tcaaacgtgggcaactttgatattggcctcatggaggtgct
ggtggagaagattttgacctggcattcatgcccgcaatga
acgctgtgctgggttctggcgtcctctcccaaaatcctc
aacatcgactttagcaatgcagacattgacgtgttggagga
ccttttggtgctgagcgcacgggtaccggtcgccaccatgg
tgagcaagggcgaggagctgttcaccggggtggtgcccatc
ctggtcgagctggacggcgacgtaaacggccacaagttcag
cgtgtccggcgagggcgagggcgatgccacctacggcaagc
tgaccctgaagttcatctgcaccaccggcaagctgcccgtg
ccctggcccaccctcgtgaccaccctgacctacggcgtgca
gtgcttcagccgctaccccgaccacatgaagcagcacgact
tcttcaagtccgccatgcccgaaggctacgtccaggagcgc
accatcttcttcaaggacgacggcaactacaagacccgcgc
cgaggtgaagttcgagggcgacaccctggtgaaccgcatcg
agctgaagggcatcgacttcaaggaggacggcaacatcctg
gggcacaagctggagtacaactacaacagccacaacgtcta
tatcatggccgacaagcagaagaacggcatcaaggtgaact
tcaagatccgccacaacatcgaggacggcagcgtgcagctc
gccgaccactaccagcagaacacccccatcggcgacggccc
cgtgctgctgcccgacaaccactacctgagcacccagtccg
ccctgagcaaagaccccaacgagaagcgcgatcacatggtc
ctgctggagttcgtgaccgccgccgggatcactctcggcat
ggacgagctgtacaagtaaagcggccgcgactctagaattc
aatcgatggccgccatggcccaacttgtttattgcagctta
taatggttacaaataaagcaatagcatcacaaatttcacaa
ataaagcatttttttcactgcattctagttgtggtttgtcc

Figure 1-4

```
aaactcatcaatgtatcttatcatgtctggatcgggaatta
attcggcgcagcaccatggcctgaataacctctgaaagag
gaacttggttaggtaccttctgaggcggaagaaccagctg
tggaatgtgtcagttagggtgtggaaagtcccaggctc
ccagcaggcagaagtatgcaaagcatgcatctcaattagt
cagcaaccagtgtggaaagtcccaggctcccagcaggc
agaagtatgcaaagcatgcatctcaattagtcagcaccat
agtcccgccctaactccgcccatcccgccctaactccgc
ccagttccgccattctccgcccatggctgactaattttt
tttatttatgcagaggccgaggccgcctcggcctctgagct
attccagaagtagtgaggaggcttttttggaggcctaggct
tttgcaaaagctgttaacagcttggcactggccgtcgttt
tacaacgtcgtgactgggaaaccctggcgttacccaactt
aatcgcttgcagcacatccccctttcgccagctggcgtaa
tagcgaagaggcccgcaccgatcgcccttccaacagttgc
gcagcctgaatggcgaatggcgcctgatgcggtattttctc
cttacgcatctgtgcggtatttcaccgcatacgtcaaag
caaccatagtacgcgccctgtagcggcgcattaagcgcggc
gggtgtggtggttacgcgcagcgtgaccgctacacttgcca
gcgccctagcgcccgctcctttcgctttcttccttcctt
ctcgccacgttcgccggctttccccgtcaagctctaaatcg
gggctcccttaggttccgattagtgctttacggcacc
tcgaccccaaaaacttgattgggtgatggttcacgtagt
gggccatcgccctgatagacggttttcgccctttgacgtt
ggagtccacgttcttaatagtggactcttgttccaaactg
gaacaacactcaacccatctcgggctattcttttgatta
taaggattttgccgatttcggcctattggttaaaaatga
gctgatttaacaaaattaacgcgaattttaacaaaatat
taacgtttacaatttatggtgcactctcagtacaatctgc
```

Figure 1-5 tctgatgccgcatagttaagccagccccgacaccgccaac
acccgctgacgcgcctgacgggcttgtctgctcccggcat
ccgcttacagacaagctgtgaccgtctccggagctgcatg
tgtcagaggttttcaccgtcatcaccgaaacgcgcgagacg
aaaggcctcgtgatacgcctattttataggttaatgtca
tgataataatggtttcttagacgtcaggtggcacttttcgg
ggaaatgtgcgcggaaccctatttgtttattttctaaat
acattcaaatatgtatccgctcatgagacaataaccctgat
aaatgcttcaataatattgaaaaggaagagtatgagtatt
caacattccgtgtcgcccttattcctttttgcggcatt
ttgccttcctgtttttgctcacccagaaacgctggtgaaag
taaagatgctgaagatcagttgggtgcacgagtgggttac
atcgaactggatctcaacagcggtaagatccttgagagttt
tcgccccgaagaacgttttccaatgatgagcactttaaag
ttctgctatgtggcgcggtattatcccgtattgacgccggg
caagagcaactcggtcgccgcatacactattctcagaatga
cttggttgagtactcaccagtcacagaaaagcatcttacgg
atggcatgacagtaagagaattatgcagtgctgccataacc
atgagtgataacactgcggccaacttactctgacaacgat
cggaggaccgaaggagctaaccgcttttttgcacaacatgg
gggatcatgtaactcgccttgatcgttgggaaccggagctg
aatgaagccataccaaacgacgagcgtgacaccacgatgcc
tgtagcaatggcaacaacgttgcgcaaactattaactggcg
aactacttactctagcttcccggcaacaattaatagactgg
atggaggcggataaagttgcaggaccacttctgcgctcggc
ccttccggctgctggtttattgctgataaatctggagccg
gtgagcgtgggtctcgcggtatcattgcagcactggggcca
gatggtaagccctcccgtatcgtagttatctacacgacggg
gagtcaggcaactatggatgaacgaaatagacagatcgctg

Figure 1-6

```
agataggtgcctcactgattaagcattggtaactgtcagac
caagttactcatatactttagattgattaaaacttca
tttttaatttaaaggatctaggtgaagatccttttgata
atctcatgaccaaatccttaacgtgagttttcgttccac
tgagcgtcagacccgtagaaagatcaaggatcttcttg
agatcctttttctgcgcgtaatctgctgcttgcaaacaa
aaaaccaccgctaccagcggtggtttgtttgccggatcaa
gagctaccaactcttttccgaaggtaactggcttcagcag
agcgcagataccaaatactgttcttctagtgtagccgtagt
taggccaccacttcaagaactctgtagcaccgcctacatac
ctcgctctgctaatcctgttaccagtggctgctgccagtgg
cgataagtcgtgtcttaccgggttggactcaagacgatagt
taccggataaggcgcagcggtcggctgaacggggggttcg
tgcacagcccagcttggagcgaacgacctacaccgaact
gagataccacagcgtgagctatgagaaagcgccacgcttc
ccgaagggagaaagcggacaggtatccggtaagcggcagg
gtcggaacaggagagcgcacgaggagcttcaggggaaa
cgcctggtatctttatagtcctgtcgggtttcgccacctct
gacttgagcgtcgattttgtgatgctcgtcaggggggcgg
agcctatggaaaaacgccagcaacgcggccttttacggtt
cctggccttttgctggccttttgctcacatgttctttcctg
cgttatcccctgattctgtggataaccgtattaccgcctt
gagtgagctgataccgctcgccgcagccgaacgaccgagcg
cagcgagtcagtgagcgaggaagcggaagagcgcccaatac
gcaaaccgcctctccccgcgcgttggccgattcattaatgc
agctggcacgacaggtttcccgactggaaagcgggcagtga
gcgcaacgcaattaatgtgagttagctcactcattaggcac
cccaggctttacactttatgcttccggctcgtatgttgtgt
ggaattgtgagcggataacaatttcacacaggaaacagcta
tgacatgattacgaattaa
```

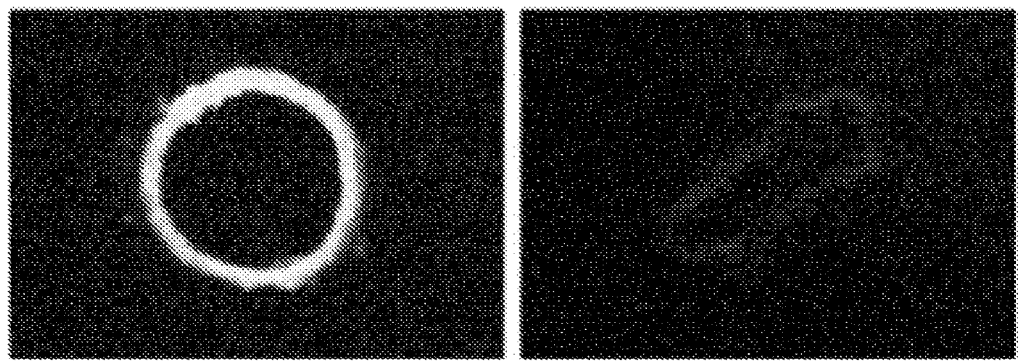
Figure 2
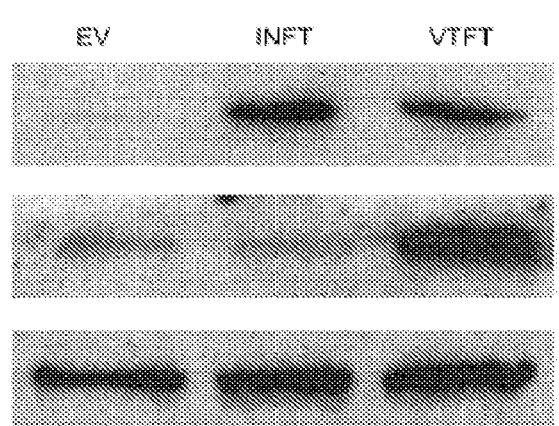
Figure 3
Figure 3a
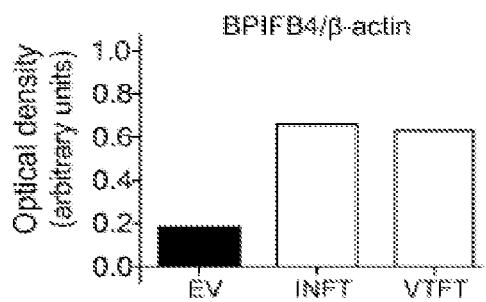
Figure 3b
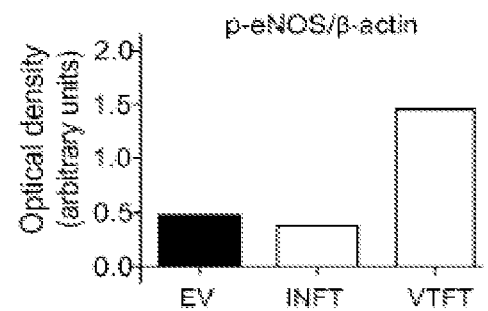
Figure 3c

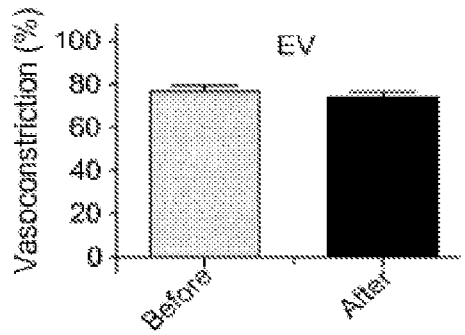
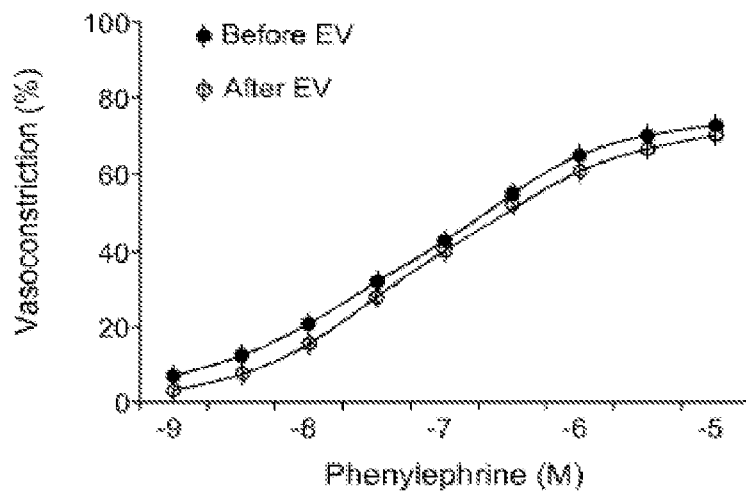
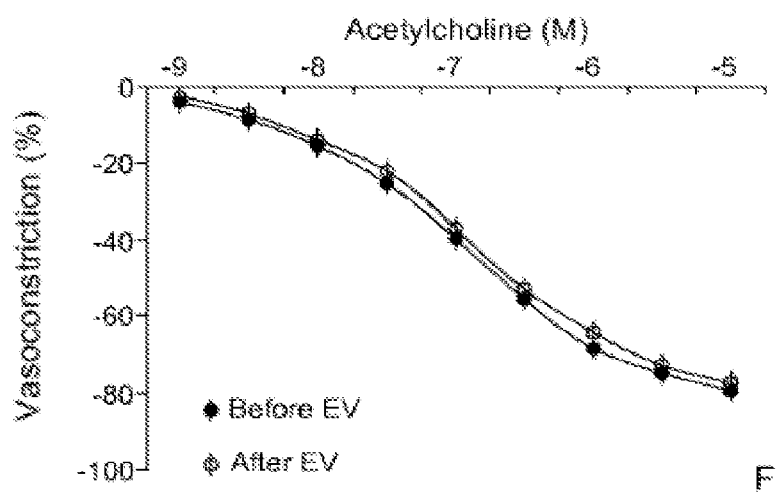
Figure 4

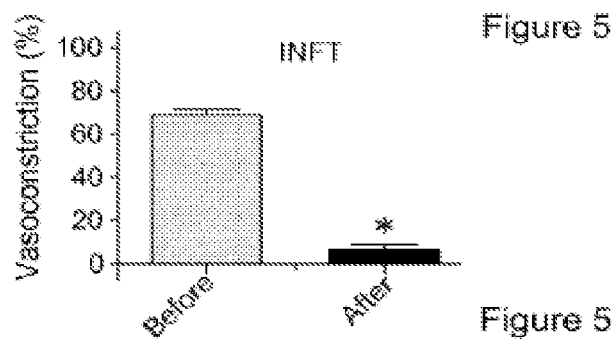
Figure 5a
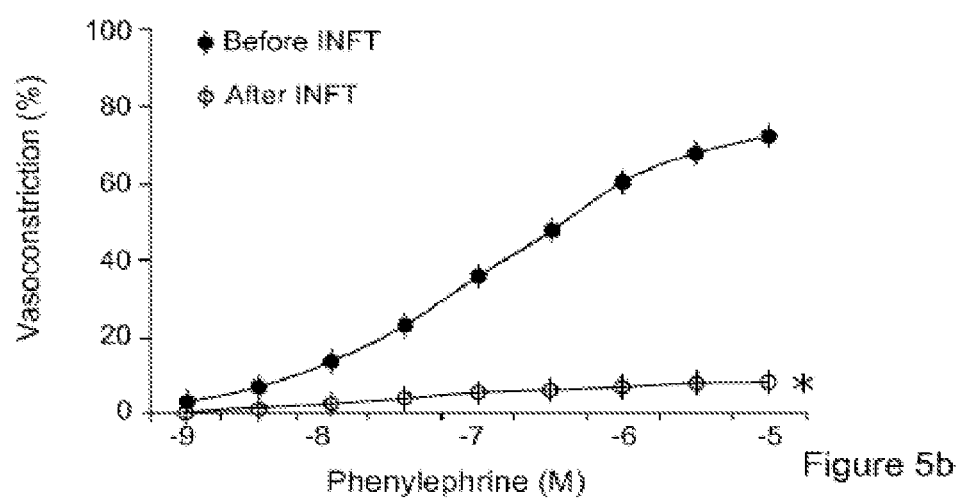
Figure 5b
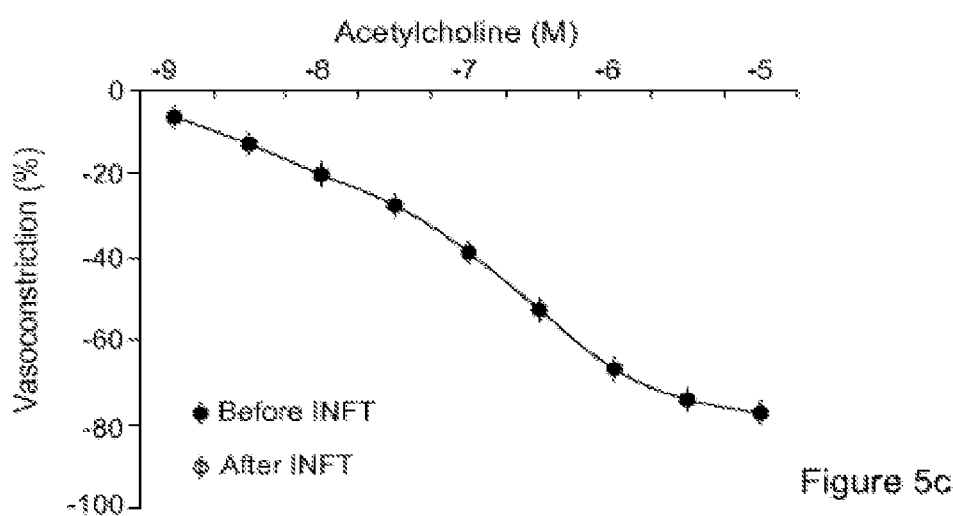
Figure 5c
Figure 5

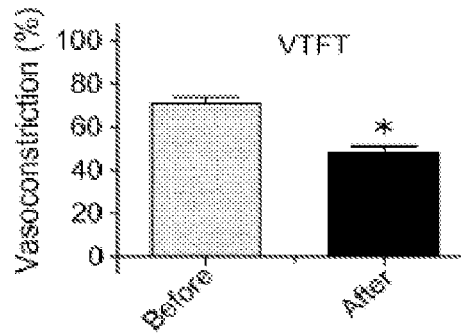
Figure 6a
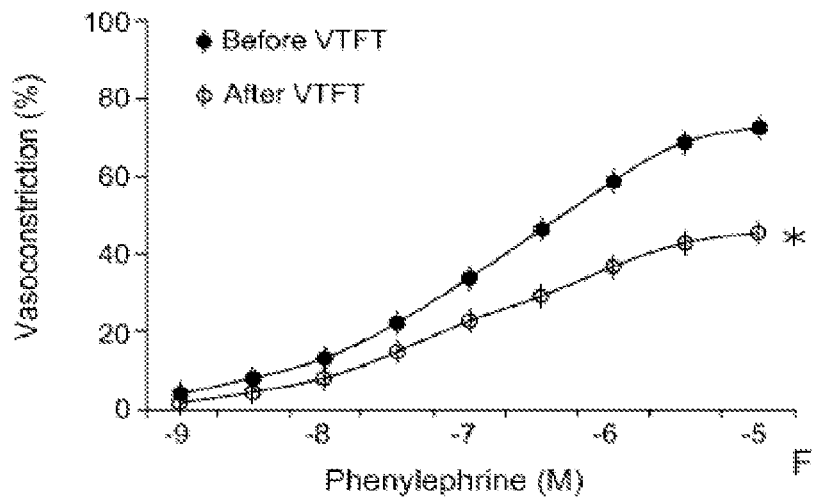
Figure 6b
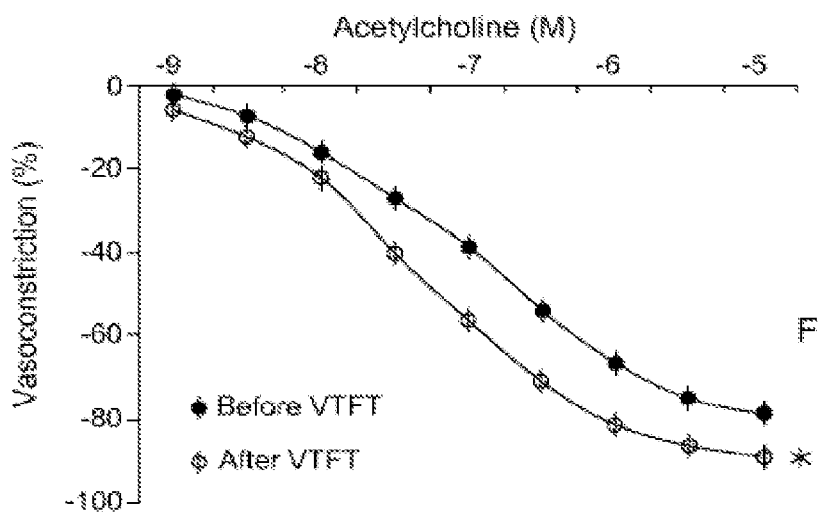
Figure 6c
Figure 6

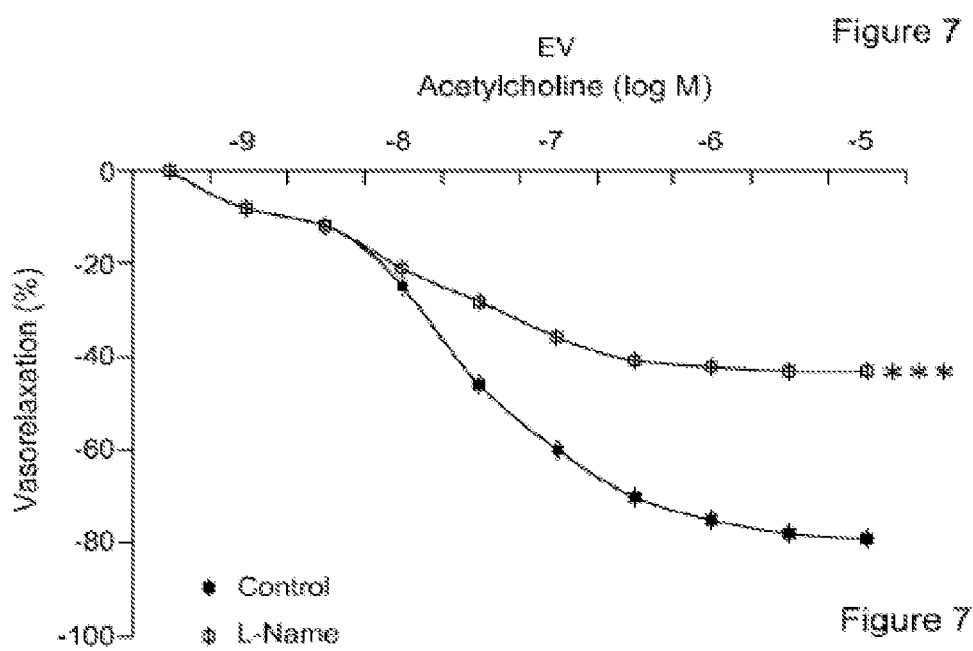
Figure 7a
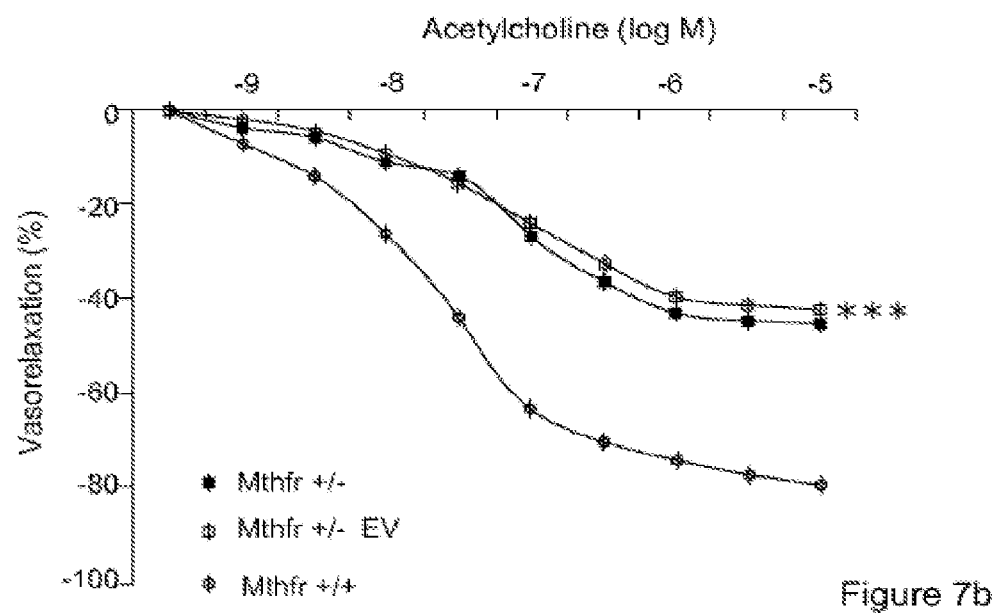
Figure 7b
Figure 7

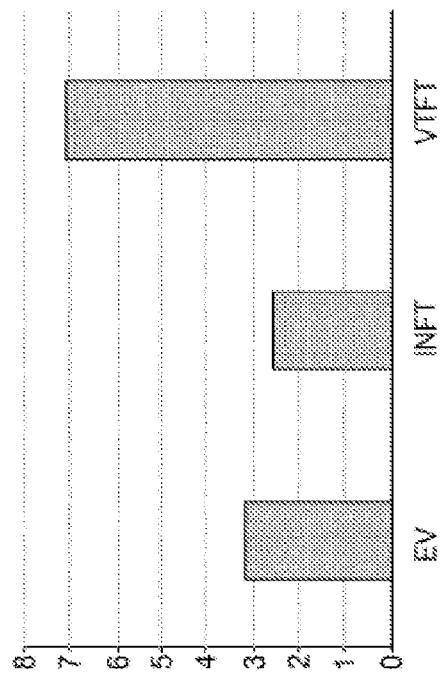
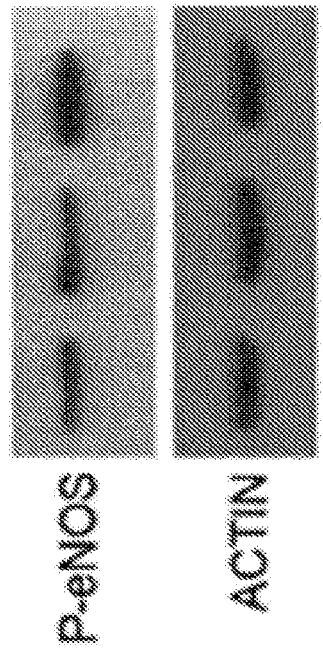
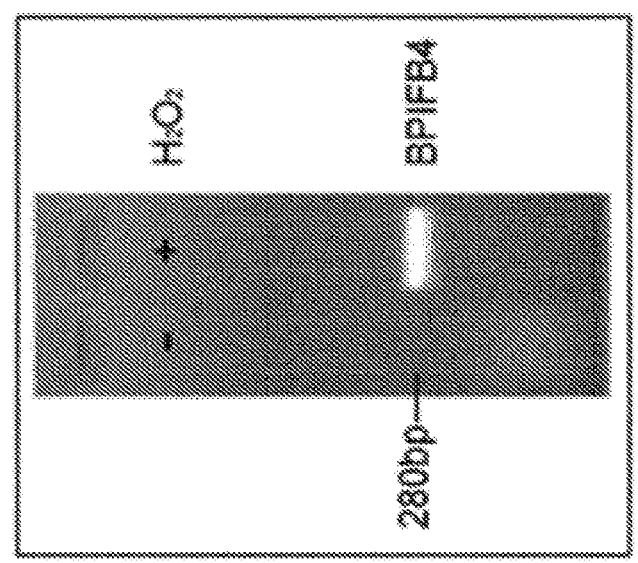
Figure 9

VARIANT OF A BPIFB4 PROTEIN

CROSS-REFERENCE TO RELATED APPLICATIONS

This application is a continuation of U.S. patent application Ser. No. 16/511,051, filed Jul. 15, 2019, which is a continuation of U.S. patent application Ser. No. 14/655,651, filed Jun. 25, 2015, now abandoned, which is a national stage filing under 35 USC § 371 of International PCT Application number PCT/EP2013/078076, filed Dec. 27, 2013, which claims priority from European Patent Application No 12425208.1 filed Dec. 28, 2012. The entire disclosures of each of the foregoing applications are incorporated by reference in their entirety.

FIELD OF THE INVENTION

The present invention relates to a variant of BPIFB4 protein (Bactericidal/Permeability Increasing protein family B, member 4) and to a polynucleotide or a vector encoding said variant of BPIFB4 protein and to their use for the treatment of pathologies associated with endothelial dysfunction due to impaired eNOS and NO mediated vasodilatation.

BACKGROUND OF THE INVENTION

Human BPIFB4 (also known as C20orf186; RY2G5; LPLUNC4) is a secreted protein member of the BPI/LBP/PLUNC-like family, which has been implicated in host defence processes against bacteria. The protein exists as two different isoforms of different length with amino acid sequences of 575 (Acc. P-59827-2) and 613 (Acc. EAW76337.1) amino acids (Bingle C D et al, Biochem Soc Trans. (2011) 39 (4): 977-83; Andrault J.-B et al, Genomics (2003) 82: 172-184; Bingle C. D et al., Hum. Mol. Genet. (2002) 11: 937-943; Bingle C. D et al, Protein Sci. (2004) 13: 422-430).

A number of single nucleotide polymorphisms have been described for this protein at the following sites, indicated with reference to the 575 amino acid sequence: rs2070325-Ile229Val, rs 571391-Asn281Thr, rs7583529Phe488Leu and rs285097-Thr494Ile, that may lead to the generation of a number of different variants of the protein. The present inventors have identified and characterised a number of variants of BPIFB4. After a careful analysis of the haplotype phases (i.e. combination of the alleles) of the four polymorphisms described above, the present inventors have found that the most common haplotype (65% analyzed chromosomes) is the combination AACT that codify for amino acids Ile229/Asn281/Leu488/Ile494 (INLI); the second most frequent haplotype is the combination GCTC (30% chromosomes contain this haplotype) that codify for amino acids Val229/Thr281/Phe488/Thr494 (VTFT) and finally the combination of AATC is represented only in 2% of human Caucasian chromosomes that codify for Ile229/Asn281/Phe488/Thr494 (INFT).

The vascular endothelium is formed by a layer of cells located between the vessel lumen and the vascular smooth muscle cells. These cells continuously produce nitric oxide (NO), a soluble gas that is synthesized by the enzyme endothelial nitric oxide synthase (eNOS). This substance has a crucial role in the regulation of vascular homeostasis and endothelial function, including modulation of the vascular tone, regulation of local cell growth, and protection of the vessel from injurious consequences of platelets and cells circulating in blood.

A growing list of conditions have been associated with a decreased release of nitric oxide by the arterial wall either because of impaired synthesis by eNOS or excessive oxidative degradation (American Journal of Physiology, Endocrinology and metabolism 2012 Mar. 1; 302(5) and Current Vascular Pharmacology 2012 January; 10(1): pages 4-18). Most of these pathological conditions are associated with aging. For example, impairment of Nitric Oxide signalling has been reported in coronary spastic angina (Miyamoto Y et al. Hum Mol Genet. 2000 Nov. 1; 9(18): pages 2629-37), thrombosis (Loscalzo J, Circulation Research. 2001; 88, pages 756-762), Pulmonary hypertension (D'Uscio L D., Cardiovasc Res 2011, 92 (3), pages 359-360), pre-eclampsia (The Lancet, Volume 361, 9368, Pages 1511-1517), vasculites (Kanwar J R et al., Curr Med Chem. 2009; 16(19): 2373-2394), cancer (Kanwar J R et al. Curr Med Chem. 2009; 16(19): pages 2373-2394), inflammatory disorders (Kanwar J R et al., Curr Med Chem. 2009; 16(19): pages 2373-2394), venus insufficiency (Förstermann U et al. Circulation. 2006; 113: pages 1708-1714), in genetic diseases with reduced eNOS activity and NO production, for example as for MTHFR gene variations (Lemarie C A et al., Am J Physiol Heart Circ Physiol 2011, vol. 300: H745-53), arterial hypertension (Sparacino-Watkins C E et al, Circulation., 2012; vol 125(23), pages 2824-6; Böger R H et al, Circulation. 2009, vol 119(12), pages 1592-600), atherosclerosis, diabetes mellitus, dyslipidemia, renal failure (Jiang B et al, Hum Gene Ther. 2012; 23(11), pages 1166-75 Ponnuswamy Pet al. PLoS One. 2012; 7(1):e30193; Vita J A. et al, Circulation. 2011, Vol 124(25), pages 906-12; Li Z L et al., PLoS One. 2012, Vol 7(6):e38787), metabolic syndrome (Quyyumi A A et al., Circulation. 1995, Vol 92: pages 320-326), stroke (Madden J A., Neurology. 2012 Sep. 25; 79(13 Suppl 1):558-62), myocardial Infarction (Nakata S et al, Circulation. 2008 Apr. 29; Vol 117(17): pages 2211-23), erectile dysfunction (Bianca R d et., PLoS One. 2012, Vol 7(2): e31019), neurodegenerative diseases and multiple sclerosis (Faraci F M., Circulation Research. 2006, Volume 99, pages 1029-1030; Wu M, et al, Glia. 2009, Vol 57(11), pages 1204-15), cognitive disorders (Rayatnia et al, Eur J Pharmacol. 2011, Vol 666(1-3), pages 122-30; Paydar et al, Brain Res. 2011; Vol 1386, pages 89-99), retinal degeneration, uveoretinitis, vascular retinopathy, cataract and glaucoma (Chiou g et al. Journal of Ocular Pharmacology and Therapeutics. April 2001, 17(2): pages 189-198, Li Q et al, Invest Ophthalmol Vis Sci. 2010 October, 51(10): pages 5240-6, Kwak H J et al, Mol Cells. 2001 Oct. 31; 12(2): pages 178-84).

The decreased production of NO and the consequent disequilibrium in endothelial function has been identified as one of the key factors responsible of the above pathological states. Thus, there have been efforts in the art to identify potential candidate therapies to reverse endothelial dysfunction by enhancing the release of nitric oxide from the endothelium.

Furthermore, an increase in eNOS activity/NO production has been demonstrated to be beneficial in post-exercise fatigue in muscular dystrophy patients (Nature. 2008 Nov. 27; 456, pages 511-515) and in the implantation of stents for vascular occlusions (Sharif F, et al. Mol Ther. 2008 October; 16(10): pages 1674-80.). The present inventors have now surprisingly identified that a specific variant of the BPFIB4 protein is associated with exceptional longevity. The inventors have further found that the variant identified is surprisingly able to increase the activation of eNOS and the production of NO in endothelial cells. These biological properties are dependent by the presence in the protein of four specific amino acids at positions 229, 281, 488 and 494 since replacement of any of these positions with different amino acids leads to loss of activity of the protein.

SUMMARY OF THE INVENTION

Accordingly, the present invention provides a protein, which is a variant of a BPIFB4 protein, having an amino acid sequence with at least 85% homology to the amino acid sequence of SEQ ID NO: 1, wherein said sequence comprises a Valine at the position corresponding to position 229 of SEQ ID NO: 1, a Threonine at the position corresponding to position 281 SEQ ID NO: 1, a Phenylalanine at a position corresponding to position 488 of SEQ ID NO: 1 and a Threonine at position corresponding to position 494 of SEQ ID NO: 1.

Said homology in the amino acid sequence is preferably of at least 90%, more preferably of at least 95% and even more preferably of at least 99%.

According to a particularly preferred embodiment, the protein of the invention has the amino acid sequence of SEQ ID NO: 1.

According to an alternative preferred embodiment, the protein of the invention has an amino acid sequence corresponding to the sequence of SEQ ID NO 1, wherein one or more amino acids at positions different from positions 229, 281, 488 and 494 of SEQ ID NO 1 have been substituted by a conserved amino acid. By "conserved amino acid" it is meant an amino acid with functionally physicochemical properties equivalent to those of the original amino acid.

The invention further provides a polynucleotide having a nucleotide sequence coding for the above protein and a vector containing said polynucleotide operatively linked to expression control sequences. According to a preferred embodiment, said polynucleotide has the sequence of SEQ ID NO: 2.

There is also provided a host cell that has been transformed with the above vector and it is able to express the protein of the invention.

The invention also provides the above protein, polynucleotide or vector for use in therapy.

In particular, object of the invention is the above protein, polynucleotide or vector for use in the prevention, reduction of the risk of, amelioration and/or treatment of endothelial dysfunctions due to a decrease in the activity of eNOS and/or in the production of NO or of pathologies or conditions where it is beneficial to increase the activity of eNOS and/or the production of NO. According to a preferred embodiment, the above protein, polynucleotide or vector is for use in the prevention, reduction of the risk, amelioration or treatment of a pathology or condition selected from arterial hypertension, atherosclerosis, diabetes mellitus, dyslipidemia, renal failure, metabolic syndrome, stroke, myocardial Infarction, erectile dysfunction, neurodegenerative diseases, multiple sclerosis and cognitive disorders, retinal degeneration, uveoretinitis, vascular retinopathy, cataract and glaucoma, coronary spastic angina, thrombosis, pulmonary hypertension, pre-eclampsia, vasculites, cancer, inflammatory disorders, venus insufficiency, genetic diseases with reduced eNOS activity and NO production, for example MTHFR gene variations, post-exercise fatigue in muscular dystrophy patients. According to a further preferred embodiment, the above protein, polynucleotide or vector is for use as a co-adjuvant in the implantation of one or more stents, preferably medicated, for vascular occlusions.

Finally, the present invention provides a pharmaceutical composition comprising the protein or polynucleotide of the invention in combination with pharmaceutically acceptable carriers and excipients.

Other features and advantages of the invention will be apparent from the following detailed description and from the claims.

BRIEF DESCRIPTION OF THE FIGURES

FIGS. 1(1-1, 1-2, 1-3, 1-4, 1-5 and 1-6) shows the sequence of the pRK5 vector encoding INFT hBPIFB4 (SEQ ID NO: 3) or VTFT hBPIFB4 (SEQ ID NO:1) used in Example 3, with the sequence of the BPIFB4 protein underlined and that of EGFP in italics.

FIG. 2 shows detection of green fluorescent protein in mesenteric vessels perfused ex vivo with a plasmid encoding INFT BPIFB4 (left panel) or a control empty pRK5 plasmid (right panel) in Example 3.

FIG. 3 represents BPIFB4 protein expression and eNOS activation in mesenteric vessels perfused with empty vector (EV), a plasmid encoding INFT hBPIFB4 or VTFT hBPIFB4. Panel 3a shows a Western blot of seven pooled experiments and detection of BPIFB4 (top) and P-eNOS S1177 (middle) (FIG. 3a). Panel 3b shows quantification of BPIFB4 expression (FIG. 3b) and panel 3c shows quantification of phosphorylation at serine 1177 of eNOS (FIG. 3c).

FIGS. 4, 5 and 6: panels 4a, 5a and 6a represent KCl induced vasoconstriction observed in Example 3 in mesenteric vessels perfused ex vivo with an empty plasmid pRK5 plasmid (EV/FIG. 4a), a pRK5 plasmid encoding INFT hBPIFB4 (INFT/FIG. 5a), or a pRK5 plasmid encoding VTFT hBPIFB4 (VTFT/FIG. 6a). Panels 4b, 5b and 6b represents Phenylephrine induced vasoconstriction observed in Example 3 in mesenteric vessels perfused ex vivo with an empty plasmid pRK5 plasmid (EV/FIG. 4b), a pRK5 plasmid encoding INFT hBPIFB4 (INFT/FIG. 5b) or a pRK5 plasmid encoding VTFT hBPIFB4 (VTFT/FIG. 6b). Panels 4c, 5c and 6c represent acetylcoline induced vasodilatation observed in Example 3 in mesenteric vessels perfused ex vivo with an empty plasmid pRK5 plasmid (EV/FIG. 4c), a pRK5 plasmid encoding INFT hBPIFB4 (INFT/FIG. 5c) or a pRK5 plasmid encoding VTFT BPIFB4 (VTFT hBPIFB4/FIG. 6c). The results observed with the plasmid encoding VNFT hBPIFB4 (SEQ ID NO: 4), ITFT hBPIFB4 (SEQ ID NO: 5), VTLI hBPIFB4 (SEQ ID NO: 6) and INLI hBPIFB4 (SEQ ID NO: 7) observed on KCl induced vasoconstriction, phenylephrine induced vasoconstriction or acetylcoline induced vasodilatation in mesenteric vessels perused are superimposable to those obtained with the empty vector. (data not shown).

FIGS. 7 and 8: panels 7a and 8a represent the effect of the eNOS inhibitor L-NAME on acetylcholine-induced relaxation of vessels perfused ex vivo or with an empty pRK5 plasmid (EV/FIG. 7a) or a pRK5 plasmid encoding mutated VTFT hBPIFB4 (VTFT/FIG. 8a). Panels 8b represents recovery of vasorelaxation of vessels from methylenetetrahydrofolate reductase knockout mice (Mthfr$^{+/-}$) control (Mthfr$^{+/+}$) and knockout mice treated with either empty pRK5 plasmid ((Mthfr+/−−EV) (FIG. 7b) or a pRK5 plasmid encoding VTFT hBPIFB4 ((Mthfr$^{+/-}$−M) (FIG. 8b).

FIG. 9: panel 9a) shows a RT-PCR demonstrating induction of expression of BPIFB4 by $H_2O_2$ in HEK293T cells (FIG. 9a). Panel 9b), shows a Western blot of the phosphorylation on eNOS at Ser1177 in HEK293T cells expressing VTFT hBPIFB4 (VTFT) and in cells overexpressing INFT hBPIFB4 (INFT) or those exposed to an empty vector (EV) (FIG. 9b). Panel 9c), top, shows β-actin-normalized ODs (FIG. 9c).

DETAILED DESCRIPTION OF THE INVENTION

Figure 8A:
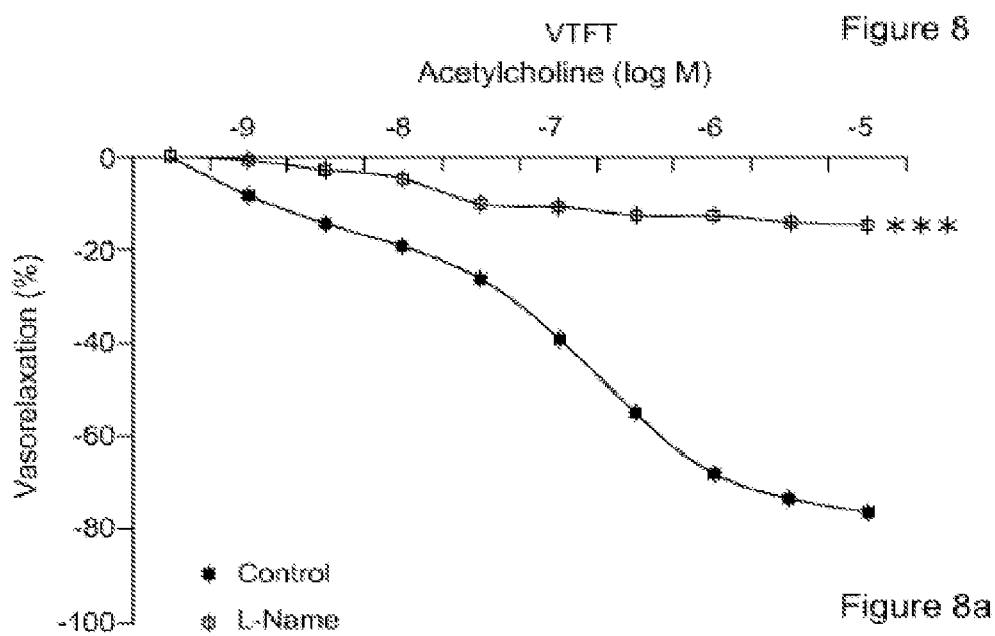

A first object of the present invention is a BPIFB4 protein variant, having an amino acid sequence with at least 85% homology to the amino acid sequence of SEQ ID NO: 1 and characterised in that said sequence comprises a Valine at the position corresponding to position 229 of SEQ ID NO: 1 (hereinafter referred to as Valine 229), a Threonine at the position corresponding to position 281 SEQ ID NO: 1 (hereinafter referred to as Threonine 281), a Phenylalanine at a position corresponding to position 488 of SEQ ID NO: 1 (hereinafter referred to as Phenylalanine 488) and a Threonine at position corresponding to position 494 of SEQ ID NO: 1 (hereinafter referred to as Threonine 494).

Said homology is preferably of at least 90%, more preferably of at least 95%, even more preferably of at least 99%.

The amino acid sequence of the BPIFB4 protein variant of the invention may differ from that of SEQ ID NO: 1 for the presence of additions, deletions or further substitutions of amino acids.

However, an essential feature of the variant of the invention is that it contains the above said four amino acids. In case of homologs that differ from SEQ ID NO: 1 for deletions or additions of amino acids, the above four amino acids are present at the position that correspond to its original position in SEQ ID NO:1. In case of homologs that differ from SEQ ID NO: 1 for substitution of amino acids, the above four amino acids are present in the same position as in SEQ ID NO: 1. According to a preferred embodiment, the protein of the invention has an amino acid sequence corresponding to SEQ ID NO 1, wherein one or more amino acids at positions different from positions 229, 281, 488 and 494 of SEQ ID NO 1 have been substituted by a conserved amino acid. By "conserved amino acid" it is meant an amino acid with functionally physicochemical properties equivalent to those of the original amino acid.

Particularly preferred proteins according to the invention have the amino acid sequence of known BPIFB4 proteins identified in *Homo Sapiens* (Acc. N. NP-59827.2; SEQ ID NO: 1 or Acc. N. NP-872325.2, corresponding to a longer isoform), *Felis Catus* (Acc N. XP003983665.1); *Pan Troglodytes* (Acc N XP525303); *Samiri boliviensis boliviensis* (Acc N XP-003932113.1); *Macaca Mulatta* (Acc N NP-001230192.1); *Pan paniscus* (Acc N. XP-003814776.1); *Otolemur garnettii* (Acc N. XP_003788148.1); *Pongo abelii* (Acc N XP-003780649.1.); *Sarcophilus harrisii* (Acc N. XP-003758987.1); *Rattus norvegicus* (Acc N. NP-001102679.2); *Callithrix jacchus* (Acc N. XP-003732841.1); *Mus musculus* (Acc N. NP-001030047.2); *Bos Taurus* (Acc N XP-003586861.1); *Canis lupus familiaris* (Acc N. XP-534383.3); *Sus scrofa* (Acc N. XP-003134448.3); *Gallus gallus* (Acc No XP-425718), *Didelphis virginiana* (L00100032880) or *Xenopus* (L00100485776), which has been modified so that it comprises a Valine at the position corresponding to position 229 of SEQ ID NO:1, a Threonine at the position corresponding to position 281 SEQ ID NO: 1, a Phenylalanine at the position corresponding to position 488 of SEQ ID NO: 1 and a Threonine at the position corresponding to position 494 of SEQ ID NO: 1.

According to a particularly preferred embodiment the BPIFB4 protein variant of the invention has the sequence of SEQ ID NO:1. A protein having such sequence will be hereinafter called VTFT hBPIFB4.

A second object of the present invention is a protein having a sequence which consist of the amino acid sequence of a BPIFB4 protein variant according to the invention linked to an additional amino acid sequence able to impart to the protein particularly advantageous properties. Preferably, said additional amino acid sequence is useful for identifying the BPIFB4 protein variant according to the invention or to target the BPIFB4 protein variant of the invention to a specific organ or tissue. Preferably said protein is a chimeric protein.

As will be described in details in the experimental section, the present inventors have surprisingly found that the above VTFT hBPIFB4 is associated with exceptional longevity in three independent populations. The present inventors have further demonstrated that the beneficial effect of the mutant protein on life expectancy is a consequence of its ability to modulate vascular dysfunctions associated with aging. As demonstrated in the experimental section, this modulation is dependent on the presence of the specific four amino acids at positions corresponding to positions 229, 281, 488 and 494 of SEQ ID NO:1 in the VTFT hBPIFB4 of the invention.

As shown in Example 3, mouse mesenteric vessels were perfused ex vivo with an empty plasmid or a plasmids encoding VTFT hBPIFB4 or proteins that differ from VTFT hBPIFB4 in that they show various substitutions at the 4 relevant amino acids: INFT hBPIFB4, having the amino acid sequence of SEQ ID NO: 3, which differs from that of VTFT hBPIFB4 in that it contains Isoleucin and an Aspargin at positions 229 and 281, respectively, VNFT hBPIFB4, having the amino acid sequence of SEQ ID NO: 4, which differs from that of VTFT hBPIFB4 in that it contains an Aspargin at position 281, ITFT hBPIFB4, having the amino acid sequence of SEQ ID NO: 5, which differs from that of VTFT hBPIFB4 in that it contains Isoleucine at position 229, VTLI hBPIFB4, having the amino acid sequence of SEQ ID NO: 6, which differs from that of VTFT hBPIFB4 in that it contains an Leucin at position 488 and a Isoleucin at position 494, INLI hBPIFB4, having the amino acid sequence of SEQ ID NO: 7, which differs from that of VTFT hBPIFB4 in that it contains in that it contains Isoleucin at positions 229, Aspargin at positions 281, Leucin at position 488 and a Isoleucin at position 494. While VNFT hBPIFB4, ITFT hBPIFB4, VTLI hBPIFB4 and INLI hBPIFB4 did not show any effect on vascular function and INFT hBPIFB4 strongly inhibited any vascular function, blocking both vasoconstriction and vasodilatation, the VTFT BPIFB4 protein showed a weak effect on inhibition of vasoconstriction and a significant enhancement of vasodilatation. This effect has been demonstrated to be mediated by activation of eNOS through phosphorylation on serine 1177 and it is therefore associated to an increase in the release of NO by endothelial cells. The ability of VTFT hBPIFB4 to induce activation of eNOS has been corroborated in the cell line HEK293T (Example 5).

The above data have also been further confirmed in an animal model of vascular disease linked to impaired NO production, the heterozygotic Mthfr knockout mice, wherein the transfection of VTFT hBPIFB4 protein has been shown to restore NO release and endothelium-dependent vasodilatation response (Example 4).

A third object of the present invention is a fragment of the BPIFB4 protein variant of the invention having a sequence comprising the above said Valine 229, Threonine 281, Phenylalanine 488 and Threonine 494. Thanks to their biological activity, the above said BPIFB4 protein variant, protein or fragment of the invention may advantageously be used in the in the prevention, reduction of the risk of, amelioration and/or treatment of pathological conditions of the endothelium due to decreased production of NO or activity of eNOS or of pathologies or conditions where it is beneficial to increase the activity of eNOS and/or the production of NO.

Thus, a fourth object of the invention is the above said BPIFB4 protein variant, protein or fragment for use in therapy.

Preferably, the BPIFB4 protein variant, the protein or the fragment of the invention are for use in the prevention, reduction of the risk of, amelioration and/or treatment of an endothelial dysfunction due to release of NO from endothelial cells below the physiological levels or a decrease in the activity of eNOS or in clinical situations wherein it is beneficial to obtain an increase in the activation of eNOS and or in the production of NO. According to a preferred embodiment of the invention, said BPIFB4 protein variant, said protein or said fragment of the invention are for use in the prevention, reduction of the risk, amelioration or treatment of a pathology selected from arterial hypertension, atherosclerosis, diabetes mellitus, dyslipidemia, renal failure, metabolic syndrome, stroke, myocardial infarction, erectile dysfunction, neurodegenerative diseases, multiple sclerosis, cognitive disorders, retinal degeneration, uveoretinitis, vascular retinopathy, cataract, glaucoma, coronary spastic angina, thrombosis, pulmonary hypertension, preeclampsia, vasculites, cancer, inflammatory disorders, venus insufficiency, genetic diseases with reduced eNOS activity and NO production, for example MTHFR gene variations.

According to an alternative preferred embodiment of the invention, said BPIFB4 protein variant is for use for the improvement of post-exercise fatigue in muscular dystrophy patients and as a co-adjuvant in the implantation of one or more stents, preferably medicated, for vascular occlusions.

The BPIFB4 protein variant, the protein or the fragment according to the invention may be administered to an subject in need thereof, affected by one of the above pathologies or in the above clinical conditions, by oral, nasal, endovenous, topical-, intra- or retro-ocular administration.

Accordingly, a fifth object of the invention is a pharmaceutical composition, preferably suitable for oral, nasal-, endovenous topical-, intra- or retro-ocular administration, comprising the BPIFB4 protein variant, the protein or the fragment of the invention in admixture with pharmaceutically acceptable carriers and/or excipients. Suitable formulations for the pharmaceutical composition of the invention are well known in the art and are, for example, described in "Remington's Pharmaceutical Sciences Handbook", Mack Publishing Company, Easton, Pennsylvania, last or Babizhayev M A. Drug Testing and Analysis, Volume 4, Issue 6, pages 468-485, June 2012).

A particularly suitable pharmaceutical formulation for the administration of the BPIFB4 protein variant, the protein or the fragment according to the invention is based on synthetic copolymers, using polyamino acidic and polysaccharidic structures, able to form reversible physical complexes with the BPIFB4 protein variant, the protein or the fragment thereof by electrostatic, hydrophobic or other physical interactions, and generate nano-aggregates from which the protein or fragment is released in intact form after administration. (Diaz-Fernandez Y A et al, Biosens Bioelectron. 2010 Sep. 15; 26(1):29-35).

A sixth object of the present invention is a polynucleotide, preferably a DNA polynucleotide, coding for the amino acid sequence of the BPIFB4 protein variant, the protein or the polypeptide according to the present invention. According to a preferred embodiment, said polynucleotide has a sequence which comprises or consists in SEQ ID NO: 2 or the sequence of a fragment thereof comprising the nucleotides coding for the above said Valine 229, Threonine 281, Phenylalanine 488 and Threonine 494.

The above polynucleotide may be used in order to obtain expression of the mutated protein or polypeptide in host cells either in vitro, ex vivo or in vivo by means of a suitable expression vector comprising it.

Thus, a seventh object of the invention is a vector containing the above said polynucleotide of the invention operatively linked to expression control sequences.

According to a preferred embodiment, the BPIFB4 protein variant, the protein or the fragment of the invention is recombinantly produced in host cells transfected with the above said vector. According to this embodiment the vector of the invention in preferably one that it is suitable for high yield production of the protein or polynucleotide. For example, the pcDNA™3.3-TOPO® vector can be used for high level expression of the protein of the invention in adherent mammalian tissue culture cells following transient transfection, or high level expression of secreted protein using the FreeStyle™ MAX CHO and FreeStyle™ MAX 293 systems (Invitrogen INC.)

Thus, an eight object of the present invention are host cells transfected with the above said vector of the invention.

An ninth object of the invention is a method of recombinantly producing the BPIFB4 protein variant, the protein or the fragment according to the invention comprising culturing the above said host cells under conditions allowing expression of the BPIFB4 protein variant, the protein or the fragment and recovering said BPIFB4 protein variant, protein or fragment.

Alternatively to direct administration as such, the BPIFB4 protein variant, the protein or the fragment of the invention may be expressed in the target tissue following administration, preferably via the endovenous, subcutaneous, intraocular or retroocular route, into a subject in need thereof of a vector according to the present invention, which is suitable to induce expression in said target tissue of the mutated protein or polypeptide. The target tissue may differ depending on the pathology to be treated and may be, for example, the endothelial tissue, the tissue of the liver, heart, kidney, eye or muscle.

According to this embodiment, the vector of the invention is one that is preferably suitable for transfection of the cells of the target tissue of interest following endovenous administration.

According to a particularly preferred embodiment, said vector is a viral vector, preferably an Adenovirus vector, more preferably a vector selected from AAV serotypes 1-9 vectors, on the basis of specificity for the target tissue of interest (Varadi K, et al, Gene Ther. (2012); 19 (8):800-9; Zincarelli C et al, Mol Ther. (2008), 16(6): 1073-80, Diaz-Fernandez Y A et al, Oligonucleotides. 2010; 20(4): 191-8.).

Thus, a tenth object of the invention is the above said polynucleotide or vector of the invention for use in therapy. Preferably, said polynucleotide or vector is for use in the prevention, reduction of the risk of, amelioration or treatment of an endothelial dysfunction due to release of NO from endothelial cells below the physiological levels or a decrease in the activity of eNOS or in conditions wherein it is beneficial to obtain an increase in the activation of eNOS and or in the production of NO. According to a preferred embodiment of the invention, said polynucleotide or vector is for use in the prevention, reduction of the risk of, amelioration or treatment of a pathology or condition selected from arterial hypertension, atherosclerosis, hypertension, diabetes mellitus, dyslipidemia, renal failure, metabolic syndrome, stroke, myocardial infarction, erectile dysfunction, neurodegenerative diseases, multiple sclerosis cognitive disorders, retinal degeneration, uveoretinitis, vascular retinopathy, cataract, glaucoma, coronary spastic angina, thrombosis, pulmonary hypertension, pre-eclampsia, vasculites, cancer, inflammatory disorders, venus insufficiency, genetic diseases with reduced eNOS activity and NO production, for example MTHFR gene variations.

According to a preferred alternative preferred embodiment of the invention, said polynucleotide or vector is for use for the improvement of post-exercise fatigue in muscular dystrophy patients and as a co-adjuvant in the implantation of one or more stents, preferably medicated, for vascular occlusions.

A eleventh object of the invention is a pharmaceutical composition, preferably suitable for endovenous, subcutaneous, intraocular or retroocular administration, comprising a vector according to the invention in admixture with pharmaceutically acceptable carriers and/or excipients. Suitable formulations for the pharmaceutical composition of the invention are well known in the art. As an example, polymeric-based nano-systems or polycomplex nanosystems may be used to deliver the vector of the invention (Murano E et al, Nat Prod Commun. (2011), 6(4): 555-72, Moustafine R I et al, Int J Pharm. 2012 Oct. 3).

The mean daily dosage of the BPIFB4 protein variant, the protein or the fragment or vector of the invention will depend upon various factors, such as the seriousness of the disease and the conditions of the patient (age, sex and weight). The skilled man may use technical means well known in the art in order to find the correct dosage amount and regime to ensure optimal treatment in each particular pathological condition.

In a further aspect of the invention, a method is provided for the treatment of an endothelial dysfunction due to release of NO from endothelial cells below physiological levels or due to a decrease in the activity of eNOS or a method for the treatment of a clinical condition wherein it is beneficial to obtain an increase in the activation of eNOS or production of NO, the method comprising administering to a subject in need of said treatment a therapeutic amount of a polynucleotide or of a viral vector containing a polynucleotide encoding a BPIFB4 protein variant having an amino acid sequence with at least 95% homology to the amino acid sequence of SEQ ID NO: 1 and characterised in that said sequence comprises a Valine at the position corresponding to position 229 of SEQ ID NO: 1, a Threonine at the position corresponding to position 281 SEQ ID NO: 1, a Phenylalanine at a position corresponding to position 488 of SEQ ID NO: 1 and a Threonine at a position corresponding to position 494 of SEQ ID NO: 1, said protein variant having activity in increasing the activity of eNOS and/or the production of NO, said vector operatively linked to expression control sequences, and wherein the activity of eNOS and/or the production of NO is increased and results in the amelioration or treatment of a pathology or clinical condition selected from arterial hypertension, renal failure, erectile dysfunction, retinal degeneration, uveoretinitis, vascular retinopathy, glaucoma and pulmonary hypertension.

In one such aspect, the viral vector is selected from AAV serotypes 1-9 vectors.

In another such aspect, the vector is an adenoviral vector.

In a further particular aspect, the method comprises administering to a subject a viral vector containing a polynucleotide encoding a BPIFB4 protein variant having an amino acid sequence with at least 95% homology to the amino acid sequence of SEQ ID NO: 1 and characterised in that said sequence comprises a Valine at the position corresponding to position 229 of SEQ ID NO: 1, a Threonine at the position corresponding to position 281 SEQ ID NO: 1, a Phenylalanine at a position corresponding to position 488 of SEQ ID NO: 1 and a Threonine at a position corresponding to position 494 of SEQ ID NO: 1, said protein variant having activity in increasing the activity of eNOS and/or the production of NO, said vector operatively linked to expression control sequences.

In another further aspect, the encoded BPIFB4 protein variant is linked to a sequence useful for targeting the BPIFB4 protein variant to a specific organ or tissue.

In another further aspect, the BPIFB4 protein variant has an amino acid sequence with at least 99% homology to the amino acid sequence of SEQ ID NO: 1, the differences from the amino acid sequence of SEQ ID NO: 1 being the presence of additions, deletions or substitutions of amino acids, and characterised in that said sequence comprises a Valine at the position corresponding to position 229 of SEQ ID NO: 1, a Threonine at the position corresponding to position 281 SEQ ID NO: 1, a Phenylalanine at a position corresponding to position 488 of SEQ ID NO: 1 and a Threonine at a position corresponding to position 494 of SEQ ID NO: 1, said protein variant having activity in increasing the activity of eNOS and/or the production of NO.

In another particular aspect, the method comprises wherein the BPIFB4 protein variant has the amino acid sequence of SEQ ID NO: 1.

In another particular method aspect, the BPIFB4 protein variant has the amino acid sequence of SEQ ID NO: 1.

In an aspect of the method of the invention, the BPIFB4 protein variant sequence differs from the amino acid sequence of SEQ ID NO: 1 in deletions or substitutions of amino acids.

In another aspect of the method of the invention, the pathology or clinical condition is selected from vascular retinopathy, uveoretinitis and retinal degeneration.

In another particular aspect of the method of the invention, the BPIFB4 protein variant sequence differs from the amino acid sequence of SEQ ID NO:1 in deletions or substitutions of amino acids.

In a further aspect, a method of the invention is provided for the treatment of an endothelial dysfunction due to release of NO from endothelial cells below physiological levels or due to a decrease in the activity of eNOS or a method for the treatment of a clinical condition wherein it is beneficial to obtain an increase in the activation of eNOS or production of NO, the method comprising administering to a subject in need of said treatment a therapeutic amount of a BPIFB4 protein variant, having an amino acid sequence with at least 95% homology to the amino acid sequence of SEQ ID NO: 1, the differences from the amino acid sequence of SEQ ID NO: 1 being the presence of additions, deletions or substitutions of amino acids, and characterised in that said sequence comprises a Valine at the position corresponding to position 229 of SEQ ID NO: 1, a Threonine at the position corresponding to position 281 SEQ ID NO: 1, a Phenylalanine at a position corresponding to position 488 of SEQ ID NO: 1 and a Threonine at a position corresponding to position 494 of SEQ ID NO: 1, said protein variant having activity in increasing the activity of eNOS and/or the production of NO, and wherein the activity of eNOS and/or the production of NO is increased and results in the amelioration or treatment of a pathology or clinical condition selected from arterial hypertension, renal failure, erectile dysfunction, retinal degeneration, uveoretinitis, vascular retinopathy, glaucoma and pulmonary hypertension.

In a particular aspect, the BPIFB4 protein variant sequence differs from the amino acid sequence of SEQ ID NO:1 in deletions or substitutions of amino acids.

In another particular aspect, the BPIFB4 protein variant is linked to a sequence useful for targeting the BPIFB4 protein variant to a specific organ or tissue.

In a further aspect of the method, the pathology or clinical condition is selected from vascular retinopathy, uveoretinitis and retinal degeneration.

In another further aspect of the method, the BPIFB4 protein variant has an amino acid sequence with at least 99% homology to the amino acid sequence of SEQ ID NO: 1, the differences from the amino acid sequence of SEQ ID NO: 1 being the presence of additions, deletions or substitutions of amino acids, and characterised in that said sequence comprises a Valine at the position corresponding to position 229 of SEQ ID NO: 1, a Threonine at the position corresponding to position 281 SEQ ID NO: 1, a Phenylalanine at a position corresponding to position 488 of SEQ ID NO: 1 and a Threonine at a position corresponding to position 494 of SEQ ID NO: 1, said protein variant having activity in increasing the activity of eNOS and/or the production of NO.

In one aspect, the BPIFB4 protein variant has the amino acid sequence of SEQ. ID No: 1.

The present invention will be better illustrated by the Examples that follow, that will not be construed as being limitative of the invention.

EXAMPLES

Example 1

Identification of the VTFT hBPIFB4 Protein in Three Independent Populations

A recently published Genome Wide Association Study (GWAS) conducted on a Southern Italian Centenarian (SIC) population has identified a number of genetic variants associated with long lived individuals (Malovini et al, *Rejuvenation Research* 2011; Vol. 14(3), pages 283-291).

In order to validate the top four variations reported in that study ($p<1\times10^{-4}$) a replication attempt was carried out in a first replication cohort recruited for the German Centenary Study (Keidorp et al; Aging Cell 2011; Vol 10, pages 622-8), comprising 1447 long-living individuals (LLIs) (age range of 95-110 years, mean age 98.8 years) and 1029 younger controls (age range 60-75 years and mean age 66.8 years). Thus, two non synonymous single-nucleotide polymorphisms (SNPs), rs2070325 and rs571391, and two intronic markers, rs7583529 and rs285097, which tag the functional variants rs7917 and rs1695501, have been tested by Taqman Analysis.

In details, DNA was extracted from peripheral blood (QIAamp DNA blood midi kit, Qiagen) of the individuals and genotyped with TaqMan probe on ABI 7900HT Real Time PCR (Applied Biosystems). For the screening, the following probes were used:
hCV25757827 for rs2070325;
hCV958887 for rs571391;
hCV28993331 for rs7583529; and
hCV3073023 for rs285097.

Data analysis was performed with Sequence Detection Systems (Applied Biosystems). The statistical methods and procedures applied to the analysis of data deriving from the genome wide scan are described in Malovini A et al., Rejuvenation Res 2011, Vol. 14, pages 283-91.

Of the four variants tested, only rs2070325, which results in the amino acid change Ile229Val in BPIFB4, replicated the association observed in the SICs cohort under the recessive genetic model (OR=2.42, 95% CI=1.56-3.77, p=5.98×10-5) in this set of LLIs (OR=1.42, 95% CI=1.12-1.80, p=5.3×10-3, Bonferroni adjusted p=0.021). This variant was then tested by Taqman analysis, as described above, for association in a second set, represented by a US based collection of 1461 LLIs (age range of 91-119 years, mean age 100.8) and 526 controls (age range of 0-35 years, mean age 28.2). Logistic regression confirmed the association of the above SNP also in this second replication set (OR:1.62, 95% CI=1.15-2.27, $p=3.7\times10^{-3}$).

Meta-analysis of association results was performed by the "meta" package implemented in R (http://cran.r-project.org/web/packages/meta/index.html). Positional and functional annotation of the identified SNPs were performed by the SNPNexus on-line resource ( ).

Results from meta-analysis, combining the association statistics deriving from the evaluation of this marker in the German- and US replication sets, revealed no statistically significant heterogeneity between the ORs estimated in the two populations (Q-statistic, p>0.05; heterogeneity index, I2=0%). According to these observations, association statistics were combined assuming a fixed effects model (OR=1.49; 95% CI=1.22-1.81; p<1×10-4).

Example 2

Haplotype Analysis of the BPIFB4 Locus

Haplotype analyses revealed patterns of strong linkage disequilibrium (LD) within the BPIFB4 genomic locus, delimiting a region that is highly enriched in non-synonymous SNPs (FIG. S1 in the Supplementary Appendix). The rs2070325 variation (Ile229Val) of BPIFB4 tags rs2889732 (Asn288Thr), rs11699009 (Leu488Phe), and rs11696307 (Ile494Thr).

The three-dimensional structure of human BPIFB4 was predicted by homology modeling with the program I-TASSER, (REF: Ambrish Roy, Alper Kucukural, Yang Zhang. I-TASSER: a unified platform for automated protein structure and function prediction. Nature Protocols, vol 5, 725-738 (2010).) using as template Protein BPI from PDB (code 1 EWF) All models were considered in the visual structural analysis, performed with the program PyMOL Version 1.2r3pre, Schrödinger, LLC (Molecular Graphics System). The above analysis revealed that Ile268Val and Asn320Thr are both located in putative protein-protein interaction site. To evaluate the effects of the variations, we predicted the structure of wild-type (WT) and mutated (Ile229Val, Asn281Thr, leu488Phe, Ile494Thr) BPIFB4 proteins by homology modeling. BPIFB4 is structurally very similar to BPI and CETP, for which experimental structures are available and because of their structural similarities, we thought it reasonable to expect that BPIFB4 binds lipopolysaccharides in regions that are similar to those of the other two proteins. Our structural analysis revealed that Leu488Phe is located in a lipid-binding pocket whose size is predicted to decrease as a consequence of the mutation. The Ile494Thr mutation is located in a second lipid-binding pocket, whose hydrophobicity is decreased by the substitution. In both cases, the mutation may result in an decreased ability to bind lipids.

In contrast, Ile229Val and Asn281Thr are located far from the lipid-binding sites of the structurally homologous proteins, so they probably affect functions such as interaction with other proteins, rather than lipid binding.

Example 3

Ex Vivo Vessel Reactivity to INFT hBPIFB4 and VTFT hBPIFB4

To determine the role of the specific BPIFB4 variant identified on vessel function, we studied the effects of ex vivo transfection of mouse mesenteric vessels with a pRK5 vector encoding VTFT hBPIFB4 or proteins that differ from VTFT hBPIFB4 in that they show various substitutions at the 4 relevant amino acids: INFT hBPIFB4, having the amino acid sequence of SEQ ID NO: 3, which differs from that of VTFT hBPIFB4 in that it contains Isoleucin and an Aspargin at positions 229 and 281, respectively, VNFT hBPIFB4, having the amino acid sequence of SEQ ID NO: 4, which differs from that of VTFT hBPIFB4 in that it contains an Aspargin at position 281, ITFT hBPIFB4, having the amino acid sequence of SEQ ID NO: 5, which differs from that of VTFT hBPIFB4 in that it contains Isoleucine at position 229, VTLI hBPIFB4, having the amino acid sequence of SEQ ID NO: 6, which differs from that of VTFT hBPIFB4 in that it contains an Leucin at position 488 and a Isoleucin at position 494 and INLI hBPIFB4, having the amino acid sequence of SEQ ID NO: 7, which differs from that of VTFT hBPIFB4 in that it contains in that it contains Isoleucin at positions 229, Aspargin at positions 281, Leucin at position 488 and a Isoleucin at position 494. The sequence of the pRK5 vectors used are reported in FIG. 1 (a, sequence of the vector codifying wtBPIFB4 and GFP and b, sequence of the vector codifying VTFT hBPIFB4 and GFP)

Second-order branches of the mesenteric arterial tree of C57BL6 mice were transfected as described previously (Vecchione C et al., J Exp Med 2005; Vol. 201, pages 1217-28).

Briefly, vessels (n=7) were placed in a Mulvany pressure system filled with Krebs solution to which was added 20 µg of a pRK5 vector encoding either INFT or VTFT hBPIFB4. An empty plasmid was used as a negative control. Vessels were perfused at 100 mmHg for 1 hour then at 60 mmHg for 5 hours.

The efficiency of transfection was evaluated by the presence of green fluorescent protein (GFP) co-expression (FIG. 2) and by Western blotting.

In details, Western blot analysis was performed on protein extracts from transfected perfused vessels (n=7 for each vector). Protein extracts were separated on 10% SDS-PAGE at 100V for 1 h or on 4-12% SDS-PAGE at 100V for 2 h and then transferred to a nitrocellulose or PVDF membrane. The membranes were incubated overnight with the following primary antibodies: anti-phospho-Ser1177 eNOS (Cell Signaling, rabbit mAb, 1:1000), anti-BPIFB4 (Abcam, rabbit polyclonal Ab, 1:200), and anti-β-actin (Cell Signaling, mouse mAb, 1:3000). The membranes were washed three times and then incubated for 1 or 2 h with the secondary antibody (horseradish peroxidase-linked anti-rabbit IgG or anti-mouse IgG, Amersham Life Science) at 1:3000 dilution. The membrane was then washed four times and specific protein bands were detected with ECL Prime chemiluminescent agents (Amersham Life Science). Western blot data were analyzed using ImageJ software (developed by Wayne Rasband, National Institutes of Health, USA) to determine optical density (OD) of the bands. The OD reading was normalized to β-actin to account for variations in loading.

As shown in FIG. 3, BPIFB4 protein was abundantly detected in vessels after perfusion with either INFT hBPIFB4- or VTFT hBPIFB4-encoding plasmids both wild type and VTFT hBPIFB4 being expressed in comparable amounts. On the contrary, vessels exposed to empty plasmids expressed a low level of native BPIFB4 protein.

In addition, vessels expressing VTFT hBPIFB4 but not INFT hBPIFB4 showed a string induction of phosphorylation of eNOS on serine 1177, an activation site of the enzyme.

Vasoconstriction was assessed with KCl (80 mM) and increasing doses of phenylephrine (from $10^{-9}$M to $10^{-6}$M), as the percentage of lumen diameter change after drug administration. Vascular responses were tested before and after transfection. Endothelium-dependent and independent relaxations were assessed by measuring the dilatatory responses of mesenteric arteries to cumulative concentrations of acetylcholine (from $10^{-9}$M to $10^{-5}$M) and nitroglycerine (from $10^{-9}$M to $10^{-5}$M), respectively, in vessels precontracted with phenylephrine at a dose necessary to obtain a similar level of precontraction in each ring (80% of initial KCl-induced contraction). The maximal contraction evoked by phenylephrine was considered as the baseline for subsequent evoked vasorelaxations. Caution was taken to avoid endothelium damage: functional integrity was reflected by the response to acetylcholine ($10^{-6}$M).

Overexpression of INFT hBPIFB4 almost abolished the KCl- and phenylephrine-induced vasoconstrictions that could be elicited before exposure to the plasmids (FIG. 5a). The absence of significant vasoconstriction impeded subsequent evaluation of vasorelaxation. In contrast, expression of VTFT hBPIFB4 partially rescued the inhibitory effects exerted by INFT hBPIFB4 on KCl and phenylephrine-induced vasoconstrictions: in fact, the vascular responses evoked by the agonists were reduced when compared with those observed before perfusion but they were not abolished (FIG. 6a-6b). In addition, upon expression of VTFT hBPIFB4 there was a significant enhancement in acetylcholine-induced vessel vasodilatation compared with that observed before transfection (FIG. 6c), but no differences in nitroglycerin-evoked smooth muscle relaxation (data not shown), indicating that this effect is due to an enhancement in endothelial function. No effect on vascular function was observed with VNFT hBPIFB4, ITFT hBPIFB4, VTLI hBPIFB4 and INLI hBPIFB4.

We examined the effect of L-NAME, an eNOS inhibitor, on vessels transfected with either an empty vector (FIG. 7, panel a, EV) or VTFT hBPIFB4-encoding plasmids (FIG. 8, panel a, VTFT). As expected, L-NAME blunted the vasodilatatory effect of acetylcholine in vessels perfused with empty plasmids, and this effect was more pronounced in vessels expressing VTFT hBPIFB4, indicating the presence of more NO in this latter condition.

Example 4

Figure 8B:
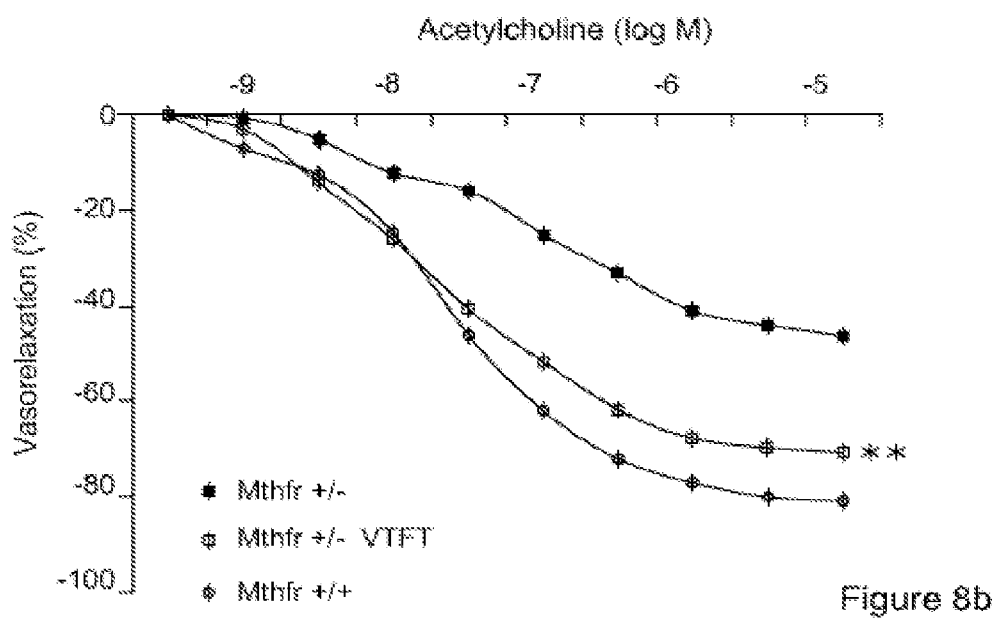

Effect of VTFT hBPIFB4 on In Vivo Model of Vascular Disease Due to Impairment of NO Release The above described experiments were also performed on mesenteric vessels from heterozygotic mthfr mice and their control, as described in Lemarie C A et al., Am J Physiol Heart Circ Physiol 2011; Vol 300:H745-53. Mthfr+/− mice show dysfunction of eNOS which is associated with the downregulation of the longevity factor surtuin 1. Thus, we explored the effect of VTFT hBPIFB4 on the mesenteric vessels of these mice. As expected, acetylcholine-induced vasorelaxation was significantly reduced in Mthfr$^{+/-}$ mice compared with Mthfr$^{+/+}$ littermates after exposure to EV (FIG. 7, panel b), but no differences were observed in nitroglycerine-evoked vascular responses (data not shown). After exposure to VTFT hBPIFB4-encoding plasmids Mthfr$^{+/-}$–VTFT, endothelial relaxation of Mthfr$^{+/-}$ vessels was significantly improved, becoming comparable to that observed in Mthfr$^{+/+}$ vessels (FIG. 8b). This indicates that VTFT hBPIFB4 may have strong therapeutic effects in fighting vascular dysfunction (FIG. 8, panel b).

Example 5

Evaluation of eNOS Modulation by BPIFB4 in Hek293T Cells

Human embryonic kidney cells (HEK293T) were maintained in Dulbecco's modified Eagle's medium (DMEM) supplemented with 10% (v/v) fetal bovine serum and 1% non-essential amino acids at 37% in a 5% CO2 atmosphere. Cells were plated at 0.25×106 per well in six-well plates, and 24 h after plating were transfected using 10 µl of Lipofectamine 2000 (LifeTechnologies) and 4 µg of plasmids. After 24 h, cells were serum-starved for 24 h. During serum starvation, transfected cells were treated with 400 µM $H_2O_2$ for 24 h. Transcription of BPIFB4 was detected by extraction from the cells of total RNA with TRIzol (Ambion), retrotranscription (iScript BioRad). cDNA was amplified with specific primers for BPIFB4 (Fw: CTCTCCC-CAAAATCCTCAACA (SEQ ID NO:8), Rev: AGCCTCTCTGGGACTGGTTC (SEQ ID NO:9)) and GAPDH (Fw: GTGAAGGTCGGAGTCAACG (SEQ ID NO:10), Rev: GGTGGAATCATATTGGAACATG (SEQ ID NO:11)).

Transcription of BPIFB4 could be induced in HEK293T cells upon exposure to $H_2O_2$: this demonstrates a role of BPIFB4 in the stress response (FIG. 9, panel a). Thus, we explored how BPIFB4 affected stress-mediated phosphorylation of eNOS on serine 1177.

Human embryonic kidney cells (HEK293T) were maintained in Dulbecco's modified Eagle's medium (DMEM) supplemented with 10% (v/v) fetal bovine serum and 1% non-essential amino acids at 37° C. in a 5% CO2 atmosphere. Cells were plated at 0.25×106 per well in six-well plates, and 24 h after plating were transfected using 10 µl of Lipofectamine 2000 (LifeTechnologies) and 4 µg of plasmids. After 24 h, cells were serum-starved for 24 h. During serum starvation, transfected cells were treated with 400 µM H2O2 for 24 h. Protein extracts were separated on 10% SDS-PAGE at 100V for 1 h or on 4-12% SDS-PAGE at 100V for 2 h and then transferred to a nitrocellulose or PVDF membrane. The membranes were incubated overnight with the following primary antibodies: anti-phospho-eNOS Ser1177 (Cell Signaling, rabbit mAb, 1:1000), and anti-β-actin (Cell Signaling, mouse mAb, 1:3000). The membranes were washed three times and then incubated for 1 or 2 h with the secondary antibody (Amersham Life Science horseradish peroxidase-linked anti-rabbit IgG or anti-mouse IgG, 1:3000). The membranes were then washed four times and specific protein bands were detected with ECL Prime chemiluminescent agents (Amersham Life Science). Western blot data were analyzed using ImageJ software (developed by Wayne Rasband, National Institutes of Health, USA) to determine optical density (OD) of the bands. The OD readings were normalized to β-actin to account for variations in loading.

As shown in FIG. 9, panel b and c, eNOS became more activated upon exposure to $H_2O_2$ in HEK293T cells expressing VTFT hBPIFB4 compared with cells overexpressing INFT hBPIFB4. This result corroborated that obtained on eNOS activation with the perfusion of vessels ex vivo.

What is claimed is:

1. An isolated polynucleotide encoding a BPIFB4 protein variant consisting of the amino acid sequence of SEQ ID NO: 1, said protein variant having activity in increasing the activity of eNOS and/or the production of NO.

2. A vector containing an isolated polynucleotide according to claim 1, operatively linked to expression control sequences.

3. The vector according to claim 2 wherein the vector is a viral vector.

4. The vector according to claim 2 wherein the vector is a viral vector selected from AAV serotypes 1-9 vectors.

5. The vector according to claim 2 wherein the vector is an adenoviral vector.

6. A pharmaceutical composition comprising an isolated polynucleotide according to claim 1 in admixture with pharmaceutically acceptable carriers and/or excipients.

7. A pharmaceutical composition according to claim 6 which is suitable for oral, nasal, endovenous, topical, subcutaneous, intraocular or retroocular administration.

8. A pharmaceutical composition comprising a vector according to claim 2 in admixture with pharmaceutically acceptable carriers and/or excipients.

9. A pharmaceutical composition according to claim 8 which is suitable for oral, nasal, endovenous, topical, subcutaneous, intraocular or retroocular administration.

10. A method for the treatment of a pathology or clinical condition, the method comprising administering to a subject in need of said treatment a therapeutic amount of an isolated polynucleotide according to claim 1, wherein the activity of eNOS or the production of NO is increased and results in the amelioration or treatment of a pathology or clinical condition, wherein the pathology or clinical condition is selected from atherosclerosis, diabetes mellitus, dyslipidemia, metabolic syndrome, stroke, myocardial infarction, neurodegenerative diseases, multiple sclerosis, cognitive disorders, coronary spastic angina, thrombosis, pre-eclampsia, vasculites, inflammatory disorders, and venus insufficiency.

11. A method for the treatment of a pathology or clinical condition, the method comprising administering to a subject in need of said treatment a therapeutic amount of a vector according to claim 2, wherein the activity of eNOS or the production of NO is increased and results in the amelioration or treatment of a pathology or clinical condition, wherein the pathology or clinical condition is selected from atherosclerosis, diabetes mellitus, dyslipidemia, metabolic syndrome, stroke, myocardial infarction, neurodegenerative diseases, multiple sclerosis, cognitive disorders, coronary spastic angina, thrombosis, pre-eclampsia, vasculites, inflammatory disorders, and venus insufficiency.

12. The isolated polynucleotide of claim 1 wherein the polynucleotide has the sequence of SEQ ID NO:2.

13. A vector containing the isolated polynucleotide according to claim 12 operatively linked to expression control sequences.

* * * * *

SEQUENCE LISTING

<160> NUMBER OF SEQ ID NOS: 11

<210> SEQ ID NO 1
<211> LENGTH: 575
<212> TYPE: PRT
<213> ORGANISM: Homo sapiens

<400> SEQUENCE: 1

```
Met Leu Gln Gln Ser Asp Ala Leu His Ser Ala Leu Arg Glu Val Pro
1               5                   10                  15

Leu Gly Val Gly Asp Ile Pro Tyr Asn Asp Phe His Val Arg Gly Pro
            20                  25                  30

Pro Pro Val Tyr Thr Asn Gly Lys Lys Leu Asp Gly Ile Tyr Gln Tyr
        35                  40                  45

Gly His Ile Glu Thr Asn Asp Asn Thr Ala Gln Leu Gly Gly Lys Tyr
    50                  55                  60

Arg Tyr Gly Glu Ile Leu Glu Ser Glu Gly Ser Ile Arg Asp Leu Arg
65                  70                  75                  80

Asn Ser Gly Tyr Arg Ser Ala Glu Asn Ala Tyr Gly Gly His Arg Gly
                85                  90                  95

Leu Gly Arg Tyr Arg Ala Ala Pro Val Gly Arg Leu His Arg Arg Glu
```

```
                100             105              110
Leu Gln Pro Gly Glu Ile Pro Pro Gly Val Ala Thr Gly Ala Val Gly
            115                 120                 125
Pro Gly Gly Leu Leu Gly Thr Gly Gly Met Leu Ala Ala Asp Gly Ile
            130                 135             140
Leu Ala Gly Gln Gly Gly Leu Leu Gly Gly Gly Leu Leu Gly Asp
145                 150                 155                 160
Gly Gly Leu Leu Gly Gly Gly Val Leu Gly Val Leu Gly Glu Gly
                165                 170                 175
Gly Ile Leu Ser Thr Val Gln Gly Ile Thr Gly Leu Arg Ile Val Glu
            180                 185                 190
Leu Thr Leu Pro Arg Val Ser Arg Leu Leu Pro Gly Val Gly Val
            195                 200                 205
Tyr Leu Ser Leu Tyr Thr Arg Val Ala Ile Asn Gly Lys Ser Leu Ile
            210                 215                 220
Gly Phe Leu Asp Val Ala Val Glu Val Asn Ile Thr Ala Lys Val Arg
225                 230                 235                 240
Leu Thr Met Asp Arg Thr Gly Tyr Pro Arg Leu Val Ile Glu Arg Cys
                245                 250                 255
Asp Thr Leu Leu Gly Gly Ile Lys Val Lys Leu Leu Arg Gly Leu Leu
            260                 265                 270
Pro Asn Leu Val Asp Asn Leu Val Thr Arg Val Leu Ala Asp Val Leu
            275                 280                 285
Pro Asp Leu Leu Cys Pro Ile Val Asp Val Val Leu Gly Leu Val Asn
            290                 295                 300
Asp Gln Leu Gly Leu Val Asp Ser Leu Ile Pro Leu Gly Ile Leu Gly
305                 310                 315                 320
Ser Val Gln Tyr Thr Phe Ser Ser Leu Pro Leu Val Thr Gly Glu Phe
                325                 330                 335
Leu Glu Leu Asp Leu Asn Thr Leu Val Gly Glu Ala Gly Gly Gly Leu
            340                 345                 350
Ile Asp Tyr Pro Leu Gly Trp Pro Ala Val Ser Pro Lys Pro Met Pro
            355                 360                 365
Glu Leu Pro Pro Met Gly Asp Asn Thr Lys Ser Gln Leu Ala Met Ser
            370                 375                 380
Ala Asn Phe Leu Gly Ser Val Leu Thr Leu Leu Gln Lys Gln His Ala
385                 390                 395                 400
Leu Asp Leu Asp Ile Thr Asn Gly Met Phe Glu Glu Leu Pro Pro Leu
                405                 410                 415
Thr Thr Ala Thr Leu Gly Ala Leu Ile Pro Lys Val Phe Gln Gln Tyr
            420                 425                 430
Pro Glu Ser Cys Pro Leu Ile Ile Arg Ile Gln Val Leu Asn Pro Pro
            435                 440                 445
Ser Val Met Leu Gln Lys Asp Lys Ala Leu Val Lys Val Leu Ala Thr
            450                 455                 460
Ala Glu Val Met Val Ser Gln Pro Lys Asp Leu Glu Thr Thr Ile Cys
465                 470                 475                 480
Leu Ile Asp Val Asp Thr Glu Phe Leu Ala Ser Phe Ser Thr Glu Gly
                485                 490                 495
Asp Lys Leu Met Ile Asp Ala Lys Leu Glu Lys Thr Ser Leu Asn Leu
            500                 505                 510
Arg Thr Ser Asn Val Gly Asn Phe Asp Ile Gly Leu Met Glu Val Leu
            515                 520                 525
```

Val Glu Lys Ile Phe Asp Leu Ala Phe Met Pro Ala Met Asn Ala Val
            530                 535                 540

Leu Gly Ser Gly Val Pro Leu Pro Lys Ile Leu Asn Ile Asp Phe Ser
545                 550                 555                 560

Asn Ala Asp Ile Asp Val Leu Glu Asp Leu Leu Val Leu Ser Ala
                565                 570                 575

<210> SEQ ID NO 2
<211> LENGTH: 1728
<212> TYPE: DNA
<213> ORGANISM: Homo sapiens
<220> FEATURE:
<221> NAME/KEY: source
<222> LOCATION: 1..1728
<223> OTHER INFORMATION: /organism="Homo sapiens"
      /mol_type="unassigned DNA"

<400> SEQUENCE: 2

| | | | | | |
|---|---|---|---|---|---|
| atgctgcagc | aaagtgatgc | tctccactcg | gccctgagag | aggtgccctt | gggtgttggt | 60 |
| gatattccct | acaatgactt | ccatgtccga | gaccccccc | cagtatatac | caacggcaaa | 120 |
| aaacttgatg | gtatttacca | gtatggtcac | attgagacca | cgacaacac | tgctcagctg | 180 |
| gggggcaaat | accgatatgg | tgagatcctt | gagtccgagg | gaagcatcag | ggacctccga | 240 |
| aacagtggct | atcgcagtgc | cgagaatgca | tatggaggcc | acaggggcct | cgggcgatac | 300 |
| agggcagcac | ctgtgggcag | gcttcaccgg | cgagagctgc | agcctggaga | aatcccacct | 360 |
| ggagttgcca | ctggggcggt | gggcccaggt | ggtttgctgg | gcactggagg | catgctggca | 420 |
| gctgatggca | tcctcgcagg | ccaaggtggc | ctgctcggcg | gaggtggtct | ccttggtgat | 480 |
| ggaggacttc | ttggaggagg | gggtgtcctg | ggcgtgctcg | gcgagggtgg | catcctcagc | 540 |
| actgtgcaag | gcatcacggg | gctgcgtatc | gtggagctga | ccctccctcg | ggtgtccgtg | 600 |
| cggctcctgc | ccggcgtggg | tgtctacctg | agcttgtaca | cccgtgtggc | catcaacggg | 660 |
| aagagtctta | ttggcttcct | ggacgtcgca | gtagaagtga | acatcacagc | caaggtccgg | 720 |
| ctgaccatgg | accgcacggg | ttatcctcgg | ctggtcattg | agcgatgtga | caccctccta | 780 |
| gggggcatca | aagtcaagct | gctgcgaggg | cttctcccca | atctcgtgga | caatttagtg | 840 |
| acccgagtcc | tggccgacgt | cctccctgac | ttgctctgcc | ccatcgtgga | tgtggtgctg | 900 |
| ggtcttgtca | tgaccagct | gggcctcgtg | gattctctga | ttcctctggg | gatattggga | 960 |
| agtgtccagt | acaccttctc | cagcctcccg | cttgtgaccg | gggaattcct | ggagctggac | 1020 |
| ctcaacacgc | tggttgggga | ggctggagga | ggactcatcg | actacccatt | ggggtggcca | 1080 |
| gctgtgtctc | ccaagccgat | gccagagctg | cctcccatgg | gtgacaacac | caagtcccag | 1140 |
| ctggccatgt | ctgccaactt | cctgggctca | gtgctgactc | tactgcagaa | gcagcatgct | 1200 |
| ctagacctgg | atatcaccaa | tggcatgttt | gaagagcttc | ctccacttac | cacagccaca | 1260 |
| ctgggagccc | tgatcccaa | ggtgttccag | cagtaccccg | agtcctgccc | acttatcatc | 1320 |
| aggatccagg | tgctgaaccc | accatctgtg | atgctgcaga | aggacaaagc | gctggtgaag | 1380 |
| gtgttggcca | ctgccgaggt | catggtctcc | cagcccaaag | acctggagac | taccatctgc | 1440 |
| ctcattgacg | tggacacaga | attcttggcc | tcatttttcca | cagaaggaga | taagctcatg | 1500 |
| attgatgcca | agctggagaa | gaccagcctc | aacctcagaa | cctcaaacgt | gggcaacttt | 1560 |
| gatattggcc | tcatggaggt | gctggtggag | aagattttg | acctggcatt | catgcccgca | 1620 |
| atgaacgctg | tgctgggttc | tggcgtccct | ctccccaaaa | tcctcaacat | cgactttagc | 1680 | aatgcagaca ttgacgtgtt ggaggacctt ttggtgctga gcgcatga                    1728

<210> SEQ ID NO 3
<211> LENGTH: 575
<212> TYPE: PRT
<213> ORGANISM: Homo sapiens

<400> SEQUENCE: 3

```
Met Leu Gln Gln Ser Asp Ala Leu His Ser Ala Leu Arg Glu Val Pro
1               5                   10                  15

Leu Gly Val Gly Asp Ile Pro Tyr Asn Asp Phe His Val Arg Gly Pro
            20                  25                  30

Pro Pro Val Tyr Thr Asn Gly Lys Lys Leu Asp Gly Ile Tyr Gln Tyr
        35                  40                  45

Gly His Ile Glu Thr Asn Asp Asn Thr Ala Gln Leu Gly Gly Lys Tyr
    50                  55                  60

Arg Tyr Gly Glu Ile Leu Glu Ser Glu Gly Ser Ile Arg Asp Leu Arg
65                  70                  75                  80

Asn Ser Gly Tyr Arg Ser Ala Glu Asn Ala Tyr Gly His Arg Gly
                85                  90                  95

Leu Gly Arg Tyr Arg Ala Ala Pro Val Gly Arg Leu His Arg Arg Glu
            100                 105                 110

Leu Gln Pro Gly Glu Ile Pro Pro Gly Val Ala Thr Gly Ala Val Gly
        115                 120                 125

Pro Gly Gly Leu Leu Gly Thr Gly Gly Met Leu Ala Ala Asp Gly Ile
    130                 135                 140

Leu Ala Gly Gln Gly Gly Leu Gly Gly Gly Leu Leu Gly Asp
145                 150                 155                 160

Gly Gly Leu Leu Gly Gly Gly Val Leu Gly Val Leu Gly Glu Gly
                165                 170                 175

Gly Ile Leu Ser Thr Val Gln Gly Ile Thr Gly Leu Arg Ile Val Glu
            180                 185                 190

Leu Thr Leu Pro Arg Val Ser Val Arg Leu Leu Pro Gly Val Gly Val
        195                 200                 205

Tyr Leu Ser Leu Tyr Thr Arg Val Ala Ile Asn Gly Lys Ser Leu Ile
    210                 215                 220

Gly Phe Leu Asp Ile Ala Val Glu Val Asn Ile Thr Ala Lys Val Arg
225                 230                 235                 240

Leu Thr Met Asp Arg Thr Gly Tyr Pro Arg Leu Val Ile Glu Arg Cys
                245                 250                 255

Asp Thr Leu Leu Gly Gly Ile Lys Val Lys Leu Leu Arg Gly Leu Leu
            260                 265                 270

Pro Asn Leu Val Asp Asn Leu Val Asn Arg Val Leu Ala Asp Val Leu
        275                 280                 285

Pro Asp Leu Leu Cys Pro Ile Val Asp Val Val Leu Gly Leu Val Asn
    290                 295                 300

Asp Gln Leu Gly Leu Val Asp Ser Leu Ile Pro Gly Ile Leu Gly
305                 310                 315                 320

Ser Val Gln Tyr Thr Phe Ser Ser Leu Pro Leu Val Thr Gly Glu Phe
                325                 330                 335

Leu Glu Leu Asp Leu Asn Thr Leu Val Gly Glu Ala Gly Gly Gly Leu
            340                 345                 350

Ile Asp Tyr Pro Leu Gly Trp Pro Ala Val Ser Pro Lys Pro Met Pro
        355                 360                 365
```

```
Glu Leu Pro Pro Met Gly Asp Asn Thr Lys Ser Gln Leu Ala Met Ser
370                 375                 380

Ala Asn Phe Leu Gly Ser Val Leu Thr Leu Leu Gln Lys Gln His Ala
385                 390                 395                 400

Leu Asp Leu Asp Ile Thr Asn Gly Met Phe Glu Glu Leu Pro Pro Leu
                405                 410                 415

Thr Thr Ala Thr Leu Gly Ala Leu Ile Pro Lys Val Phe Gln Gln Tyr
            420                 425                 430

Pro Glu Ser Cys Pro Leu Ile Ile Arg Ile Gln Val Leu Asn Pro Pro
        435                 440                 445

Ser Val Met Leu Gln Lys Asp Lys Ala Leu Val Lys Val Leu Ala Thr
    450                 455                 460

Ala Glu Val Met Val Ser Gln Pro Lys Asp Leu Glu Thr Thr Ile Cys
465                 470                 475                 480

Leu Ile Asp Val Asp Thr Glu Phe Leu Ala Ser Phe Ser Thr Glu Gly
                485                 490                 495

Asp Lys Leu Met Ile Asp Ala Lys Leu Glu Lys Thr Ser Leu Asn Leu
                500                 505                 510

Arg Thr Ser Asn Val Gly Asn Phe Asp Ile Gly Leu Met Glu Val Leu
            515                 520                 525

Val Glu Lys Ile Phe Asp Leu Ala Phe Met Pro Ala Met Asn Ala Val
530                 535                 540

Leu Gly Ser Gly Val Pro Leu Pro Lys Ile Leu Asn Ile Asp Phe Ser
545                 550                 555                 560

Asn Ala Asp Ile Asp Val Leu Glu Asp Leu Leu Val Leu Ser Ala
                565                 570                 575

<210> SEQ ID NO 4
<211> LENGTH: 575
<212> TYPE: PRT
<213> ORGANISM: Homo sapiens

<400> SEQUENCE: 4

Met Leu Gln Gln Ser Asp Ala Leu His Ser Ala Leu Arg Glu Val Pro
1               5                   10                  15

Leu Gly Val Gly Asp Ile Pro Tyr Asn Asp Phe His Val Arg Gly Pro
                20                  25                  30

Pro Pro Val Tyr Thr Asn Gly Lys Lys Leu Asp Gly Ile Tyr Gln Tyr
            35                  40                  45

Gly His Ile Glu Thr Asn Asp Asn Thr Ala Gln Leu Gly Gly Lys Tyr
        50                  55                  60

Arg Tyr Gly Glu Ile Leu Glu Ser Glu Gly Ser Ile Arg Asp Leu Arg
65                  70                  75                  80

Asn Ser Gly Tyr Arg Ser Ala Glu Asn Ala Tyr Gly Gly His Arg Gly
                85                  90                  95

Leu Gly Arg Tyr Arg Ala Ala Pro Val Gly Arg Leu His Arg Arg Glu
                100                 105                 110

Leu Gln Pro Gly Glu Ile Pro Pro Gly Val Ala Thr Gly Ala Val Gly
            115                 120                 125

Pro Gly Gly Leu Leu Gly Thr Gly Gly Met Leu Ala Ala Asp Gly Ile
        130                 135                 140

Leu Ala Gly Gln Gly Gly Leu Gly Gly Gly Leu Leu Gly Asp
145                 150                 155                 160

Gly Gly Leu Leu Gly Gly Gly Val Leu Gly Val Leu Gly Glu Gly
                165                 170                 175
```

-continued

Gly Ile Leu Ser Thr Val Gln Gly Ile Thr Gly Leu Arg Ile Val Glu
            180                 185                 190

Leu Thr Leu Pro Arg Val Ser Arg Leu Leu Pro Gly Val Gly Val
        195                 200                 205

Tyr Leu Ser Leu Tyr Thr Arg Val Ala Ile Asn Gly Lys Ser Leu Ile
    210                 215                 220

Gly Phe Leu Asp Val Ala Val Glu Val Asn Ile Thr Ala Lys Val Arg
225                 230                 235                 240

Leu Thr Met Asp Arg Thr Gly Tyr Pro Arg Leu Val Ile Glu Arg Cys
                245                 250                 255

Asp Thr Leu Leu Gly Gly Ile Lys Val Lys Leu Leu Arg Gly Leu Leu
            260                 265                 270

Pro Asn Leu Val Asp Asn Leu Val Asn Arg Val Leu Ala Asp Val Leu
        275                 280                 285

Pro Asp Leu Leu Cys Pro Ile Val Asp Val Val Leu Gly Leu Val Asn
    290                 295                 300

Asp Gln Leu Gly Leu Val Asp Ser Leu Ile Pro Leu Gly Ile Leu Gly
305                 310                 315                 320

Ser Val Gln Tyr Thr Phe Ser Ser Leu Pro Leu Val Thr Gly Glu Phe
                325                 330                 335

Leu Glu Leu Asp Leu Asn Thr Leu Val Gly Glu Ala Gly Gly Gly Leu
            340                 345                 350

Ile Asp Tyr Pro Leu Gly Trp Pro Ala Val Ser Pro Lys Pro Met Pro
        355                 360                 365

Glu Leu Pro Pro Met Gly Asp Asn Thr Lys Ser Gln Leu Ala Met Ser
    370                 375                 380

Ala Asn Phe Leu Gly Ser Val Leu Thr Leu Leu Gln Lys Gln His Ala
385                 390                 395                 400

Leu Asp Leu Asp Ile Thr Asn Gly Met Phe Glu Glu Leu Pro Pro Leu
                405                 410                 415

Thr Thr Ala Thr Leu Gly Ala Leu Ile Pro Lys Val Phe Gln Gln Tyr
            420                 425                 430

Pro Glu Ser Cys Pro Leu Ile Ile Arg Ile Gln Val Leu Asn Pro Pro
        435                 440                 445

Ser Val Met Leu Gln Lys Asp Lys Ala Leu Val Lys Val Leu Ala Thr
    450                 455                 460

Ala Glu Val Met Val Ser Gln Pro Lys Asp Leu Glu Thr Thr Ile Cys
465                 470                 475                 480

Leu Ile Asp Val Asp Thr Glu Phe Leu Ala Ser Phe Ser Thr Glu Gly
                485                 490                 495

Asp Lys Leu Met Ile Asp Ala Lys Leu Glu Lys Thr Ser Leu Asn Leu
            500                 505                 510

Arg Thr Ser Asn Val Gly Asn Phe Asp Ile Gly Leu Met Glu Val Leu
        515                 520                 525

Val Glu Lys Ile Phe Asp Leu Ala Phe Met Pro Ala Met Asn Ala Val
    530                 535                 540

Leu Gly Ser Gly Val Pro Leu Pro Lys Ile Leu Asn Ile Asp Phe Ser
545                 550                 555                 560

Asn Ala Asp Ile Asp Val Leu Glu Asp Leu Leu Val Leu Ser Ala
                565                 570                 575

<210> SEQ ID NO 5
<211> LENGTH: 575

```
<212> TYPE: PRT
<213> ORGANISM: Homo sapiens

<400> SEQUENCE: 5

Met Leu Gln Gln Ser Asp Ala Leu His Ser Ala Leu Arg Glu Val Pro
1               5                   10                  15

Leu Gly Val Gly Asp Ile Pro Tyr Asn Asp Phe His Val Arg Gly Pro
            20                  25                  30

Pro Pro Val Tyr Thr Asn Gly Lys Lys Leu Asp Gly Ile Tyr Gln Tyr
            35                  40                  45

Gly His Ile Glu Thr Asn Asp Asn Thr Ala Gln Leu Gly Gly Lys Tyr
        50                  55                  60

Arg Tyr Gly Glu Ile Leu Glu Ser Glu Gly Ser Ile Arg Asp Leu Arg
65                  70                  75                  80

Asn Ser Gly Tyr Arg Ser Ala Glu Asn Ala Tyr Gly Gly His Arg Gly
                85                  90                  95

Leu Gly Arg Tyr Arg Ala Ala Pro Val Gly Arg Leu His Arg Arg Glu
            100                 105                 110

Leu Gln Pro Gly Glu Ile Pro Pro Gly Val Ala Thr Gly Ala Val Gly
        115                 120                 125

Pro Gly Gly Leu Leu Gly Thr Gly Gly Met Leu Ala Ala Asp Gly Ile
130                 135                 140

Leu Ala Gly Gln Gly Gly Leu Leu Gly Gly Gly Leu Leu Gly Asp
145                 150                 155                 160

Gly Gly Leu Leu Gly Gly Gly Val Leu Gly Val Leu Gly Glu Gly
                165                 170                 175

Gly Ile Leu Ser Thr Val Gln Gly Ile Thr Gly Leu Arg Ile Val Glu
            180                 185                 190

Leu Thr Leu Pro Arg Val Ser Val Arg Leu Leu Pro Gly Val Gly Val
        195                 200                 205

Tyr Leu Ser Leu Tyr Thr Arg Val Ala Ile Asn Gly Lys Ser Leu Ile
210                 215                 220

Gly Phe Leu Asp Ile Ala Val Glu Val Asn Ile Thr Ala Lys Val Arg
225                 230                 235                 240

Leu Thr Met Asp Arg Thr Gly Tyr Pro Arg Leu Val Ile Glu Arg Cys
                245                 250                 255

Asp Thr Leu Leu Gly Gly Ile Lys Val Lys Leu Leu Arg Gly Leu Leu
            260                 265                 270

Pro Asn Leu Val Asp Asn Leu Val Thr Arg Val Leu Ala Asp Val Leu
        275                 280                 285

Pro Asp Leu Leu Cys Pro Ile Val Asp Val Val Leu Gly Leu Val Asn
290                 295                 300

Asp Gln Leu Gly Leu Val Asp Ser Leu Ile Pro Leu Gly Ile Leu Gly
305                 310                 315                 320

Ser Val Gln Tyr Thr Phe Ser Ser Leu Pro Leu Val Thr Gly Glu Phe
                325                 330                 335

Leu Glu Leu Asp Leu Asn Thr Leu Val Gly Glu Ala Gly Gly Gly Leu
            340                 345                 350

Ile Asp Tyr Pro Leu Gly Trp Pro Ala Val Ser Pro Lys Pro Met Pro
        355                 360                 365

Glu Leu Pro Pro Met Gly Asp Asn Thr Lys Ser Gln Leu Ala Met Ser
370                 375                 380

Ala Asn Phe Leu Gly Ser Val Leu Thr Leu Leu Gln Lys Gln His Ala
385                 390                 395                 400
```

```
Leu Asp Leu Asp Ile Thr Asn Gly Met Phe Glu Glu Leu Pro Pro Leu
                405                 410                 415

Thr Thr Ala Thr Leu Gly Ala Leu Ile Pro Lys Val Phe Gln Gln Tyr
            420                 425                 430

Pro Glu Ser Cys Pro Leu Ile Ile Arg Ile Gln Val Leu Asn Pro Pro
        435                 440                 445

Ser Val Met Leu Gln Lys Asp Lys Ala Leu Val Lys Val Leu Ala Thr
    450                 455                 460

Ala Glu Val Met Val Ser Gln Pro Lys Asp Leu Glu Thr Thr Ile Cys
465                 470                 475                 480

Leu Ile Asp Val Asp Thr Glu Phe Leu Ala Ser Phe Ser Thr Glu Gly
                485                 490                 495

Asp Lys Leu Met Ile Asp Ala Lys Leu Glu Lys Thr Ser Leu Asn Leu
            500                 505                 510

Arg Thr Ser Asn Val Gly Asn Phe Asp Ile Gly Leu Met Glu Val Leu
        515                 520                 525

Val Glu Lys Ile Phe Asp Leu Ala Phe Met Pro Ala Met Asn Ala Val
    530                 535                 540

Leu Gly Ser Gly Val Pro Leu Pro Lys Ile Leu Asn Ile Asp Phe Ser
545                 550                 555                 560

Asn Ala Asp Ile Asp Val Leu Glu Asp Leu Leu Val Leu Ser Ala
                565                 570                 575

<210> SEQ ID NO 6
<211> LENGTH: 575
<212> TYPE: PRT
<213> ORGANISM: Homo sapiens

<400> SEQUENCE: 6

Met Leu Gln Gln Ser Asp Ala Leu His Ser Leu Arg Glu Val Pro
1               5                   10                  15

Leu Gly Val Gly Asp Ile Pro Tyr Asn Asp Phe His Val Arg Gly Pro
            20                  25                  30

Pro Pro Val Tyr Thr Asn Gly Lys Lys Leu Asp Gly Ile Tyr Gln Tyr
        35                  40                  45

Gly His Ile Glu Thr Asn Asp Asn Thr Ala Gln Leu Gly Gly Lys Tyr
    50                  55                  60

Arg Tyr Gly Glu Ile Leu Glu Ser Glu Gly Ser Ile Arg Asp Leu Arg
65                  70                  75                  80

Asn Ser Gly Tyr Arg Ser Ala Glu Asn Ala Tyr Gly Gly His Arg Gly
                85                  90                  95

Leu Gly Arg Tyr Arg Ala Ala Pro Val Gly Arg Leu His Arg Arg Glu
            100                 105                 110

Leu Gln Pro Gly Glu Ile Pro Pro Gly Val Ala Thr Gly Ala Val Gly
        115                 120                 125

Pro Gly Gly Leu Leu Gly Thr Gly Gly Met Leu Ala Ala Asp Gly Ile
    130                 135                 140

Leu Ala Gly Gln Gly Gly Leu Gly Gly Gly Leu Leu Gly Asp
145                 150                 155                 160

Gly Gly Leu Leu Gly Gly Gly Val Leu Gly Val Leu Gly Glu Gly
                165                 170                 175

Gly Ile Leu Ser Thr Val Gln Gly Ile Thr Gly Leu Arg Ile Val Glu
            180                 185                 190

Leu Thr Leu Pro Arg Val Ser Val Arg Leu Leu Pro Gly Val Gly Val
```

195                 200                 205
Tyr Leu Ser Leu Tyr Thr Arg Val Ala Ile Asn Gly Lys Ser Leu Ile
    210                 215                 220
Gly Phe Leu Asp Val Ala Val Glu Val Asn Ile Thr Ala Lys Val Arg
225                 230                 235                 240
Leu Thr Met Asp Arg Thr Gly Tyr Pro Arg Leu Val Ile Glu Arg Cys
                245                 250                 255
Asp Thr Leu Leu Gly Gly Ile Lys Val Lys Leu Leu Arg Gly Leu Leu
            260                 265                 270
Pro Asn Leu Val Asp Asn Leu Val Thr Arg Val Leu Ala Asp Val Leu
        275                 280                 285
Pro Asp Leu Leu Cys Pro Ile Val Asp Val Val Leu Gly Leu Val Asn
    290                 295                 300
Asp Gln Leu Gly Leu Val Asp Ser Leu Ile Pro Leu Gly Ile Leu Gly
305                 310                 315                 320
Ser Val Gln Tyr Thr Phe Ser Ser Leu Pro Leu Val Thr Gly Glu Phe
                325                 330                 335
Leu Glu Leu Asp Leu Asn Thr Leu Val Gly Glu Ala Gly Gly Gly Leu
            340                 345                 350
Ile Asp Tyr Pro Leu Gly Trp Pro Ala Val Ser Pro Lys Pro Met Pro
        355                 360                 365
Glu Leu Pro Pro Met Gly Asp Asn Thr Lys Ser Gln Leu Ala Met Ser
    370                 375                 380
Ala Asn Phe Leu Gly Ser Val Leu Thr Leu Leu Gln Lys Gln His Ala
385                 390                 395                 400
Leu Asp Leu Asp Ile Thr Asn Gly Met Phe Glu Leu Pro Pro Leu
                405                 410                 415
Thr Thr Ala Thr Leu Gly Ala Leu Ile Pro Lys Val Phe Gln Gln Tyr
            420                 425                 430
Pro Glu Ser Cys Pro Leu Ile Ile Arg Ile Gln Val Leu Asn Pro Pro
        435                 440                 445
Ser Val Met Leu Gln Lys Asp Lys Ala Leu Val Lys Val Leu Ala Thr
    450                 455                 460
Ala Glu Val Met Val Ser Gln Pro Lys Asp Leu Glu Thr Thr Ile Cys
465                 470                 475                 480
Leu Ile Asp Val Asp Thr Glu Leu Leu Ala Ser Phe Ser Ile Glu Gly
                485                 490                 495
Asp Lys Leu Met Ile Asp Ala Lys Leu Glu Lys Thr Ser Leu Asn Leu
            500                 505                 510
Arg Thr Ser Asn Val Gly Asn Phe Asp Ile Gly Leu Met Glu Val Leu
        515                 520                 525
Val Glu Lys Ile Phe Asp Leu Ala Phe Met Pro Ala Met Asn Ala Val
    530                 535                 540
Leu Gly Ser Gly Val Pro Leu Pro Lys Ile Leu Asn Ile Asp Phe Ser
545                 550                 555                 560
Asn Ala Asp Ile Asp Val Leu Glu Asp Leu Leu Val Leu Ser Ala
                565                 570                 575

<210> SEQ ID NO 7
<211> LENGTH: 575
<212> TYPE: PRT
<213> ORGANISM: Homo sapiens

<400> SEQUENCE: 7

```
Met Leu Gln Gln Ser Asp Ala Leu His Ser Ala Leu Arg Glu Val Pro
1               5                   10                  15

Leu Gly Val Gly Asp Ile Pro Tyr Asn Asp Phe His Val Arg Gly Pro
            20                  25                  30

Pro Pro Val Tyr Thr Asn Gly Lys Lys Leu Asp Gly Ile Tyr Gln Tyr
            35                  40                  45

Gly His Ile Glu Thr Asn Asp Asn Thr Ala Gln Leu Gly Gly Lys Tyr
    50                  55                  60

Arg Tyr Gly Glu Ile Leu Glu Ser Glu Gly Ile Arg Asp Leu Arg
65                  70                  75                  80

Asn Ser Gly Tyr Arg Ser Ala Glu Asn Ala Tyr Gly Gly His Arg Gly
                85                  90                  95

Leu Gly Arg Tyr Arg Ala Ala Pro Val Gly Arg Leu His Arg Arg Glu
            100                 105                 110

Leu Gln Pro Gly Glu Ile Pro Pro Gly Val Ala Thr Gly Ala Val Gly
            115                 120                 125

Pro Gly Gly Leu Leu Gly Thr Gly Gly Met Leu Ala Ala Asp Gly Ile
            130                 135                 140

Leu Ala Gly Gln Gly Gly Leu Leu Gly Gly Gly Leu Leu Gly Asp
145                 150                 155                 160

Gly Gly Leu Leu Gly Gly Gly Val Leu Gly Val Leu Gly Glu Gly
            165                 170                 175

Gly Ile Leu Ser Thr Val Gln Gly Ile Thr Gly Leu Arg Ile Val Glu
                180                 185                 190

Leu Thr Leu Pro Arg Val Ser Val Arg Leu Leu Pro Gly Val Gly Val
            195                 200                 205

Tyr Leu Ser Leu Tyr Thr Arg Val Ala Ile Asn Gly Lys Ser Leu Ile
210                 215                 220

Gly Phe Leu Asp Ile Ala Val Glu Val Asn Ile Thr Ala Lys Val Arg
225                 230                 235                 240

Leu Thr Met Asp Arg Thr Gly Tyr Pro Arg Leu Val Ile Glu Arg Cys
                245                 250                 255

Asp Thr Leu Leu Gly Gly Ile Lys Val Lys Leu Leu Arg Gly Leu Leu
            260                 265                 270

Pro Asn Leu Val Asp Asn Leu Val Asn Arg Val Leu Ala Asp Val Leu
            275                 280                 285

Pro Asp Leu Leu Cys Pro Ile Val Asp Val Val Leu Gly Leu Val Asn
            290                 295                 300

Asp Gln Leu Gly Leu Val Asp Ser Leu Ile Pro Leu Gly Ile Leu Gly
305                 310                 315                 320

Ser Val Gln Tyr Thr Phe Ser Ser Leu Pro Leu Val Thr Gly Glu Phe
                325                 330                 335

Leu Glu Leu Asp Leu Asn Thr Leu Val Gly Glu Ala Gly Gly Gly Leu
            340                 345                 350

Ile Asp Tyr Pro Leu Gly Trp Pro Ala Val Ser Pro Lys Pro Met Pro
            355                 360                 365

Glu Leu Pro Pro Met Gly Asp Asn Thr Lys Ser Gln Leu Ala Met Ser
370                 375                 380

Ala Asn Phe Leu Gly Ser Val Leu Thr Leu Gln Lys Gln His Ala
385                 390                 395                 400

Leu Asp Leu Asp Ile Thr Asn Gly Met Phe Glu Glu Leu Pro Pro Leu
                405                 410                 415

Thr Thr Ala Thr Leu Gly Ala Leu Ile Pro Lys Val Phe Gln Gln Tyr
```

```
            420                 425                 430
Pro Glu Ser Cys Pro Leu Ile Ile Arg Ile Gln Val Leu Asn Pro Pro
            435                 440                 445

Ser Val Met Leu Gln Lys Asp Lys Ala Leu Val Lys Val Leu Ala Thr
        450                 455                 460

Ala Glu Val Met Val Ser Gln Pro Lys Asp Leu Glu Thr Thr Ile Cys
465                 470                 475                 480

Leu Ile Asp Val Asp Thr Glu Leu Leu Ala Ser Phe Ser Ile Glu Gly
                485                 490                 495

Asp Lys Leu Met Ile Asp Ala Lys Leu Glu Lys Thr Ser Leu Asn Leu
            500                 505                 510

Arg Thr Ser Asn Val Gly Asn Phe Asp Ile Gly Leu Met Glu Val Leu
        515                 520                 525

Val Glu Lys Ile Phe Asp Leu Ala Phe Met Pro Ala Met Asn Ala Val
    530                 535                 540

Leu Gly Ser Gly Val Pro Leu Pro Lys Ile Leu Asn Ile Asp Phe Ser
545                 550                 555                 560

Asn Ala Asp Ile Asp Val Leu Glu Asp Leu Leu Val Leu Ser Ala
                565                 570                 575

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
ctctccccaa aatcctcaac a                                              21

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
agcctctctg ggactggttc                                                20

<210> SEQ ID NO 10
<211> LENGTH: 19
<212> TYPE: DNA
<213> ORGANISM: Artificial Sequence
<220> FEATURE:
<223> OTHER INFORMATION: Primer

<400> SEQUENCE: 10
gtgaaggtcg gagtcaacg                                                 19

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
ggtggaatca tattggaaca tg                                             22
```